(12) United States Patent
LaBelle et al.

(10) Patent No.: US 11,083,394 B2
(45) Date of Patent: Aug. 10, 2021

(54) WEARABLE OPTICAL SENSOR FOR RESPIRATORY RATE MONITORING

(71) Applicant: Arizona Board of Regents on behalf of Arizona State University, Scottsdale, AZ (US)

(72) Inventors: Jeffrey LaBelle, Tempe, AZ (US); Alejo Chavez Gaxiola, Costa Mesa, CA (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 16/965,261

(22) PCT Filed: Jan. 25, 2019

(86) PCT No.: PCT/US2019/015209
§ 371 (c)(1),
(2) Date: Jul. 27, 2020

(87) PCT Pub. No.: WO2019/147978
PCT Pub. Date: Aug. 1, 2019

(65) Prior Publication Data
US 2020/0390365 A1   Dec. 17, 2020

Related U.S. Application Data

(60) Provisional application No. 62/622,500, filed on Jan. 26, 2018.

(51) Int. Cl.
*A61B 5/08* (2006.01)
*A61B 5/00* (2006.01)
*A61B 5/113* (2006.01)

(52) U.S. Cl.
CPC .......... *A61B 5/0816* (2013.01); *A61B 5/0004* (2013.01); *A61B 5/1135* (2013.01);
(Continued)

(58) Field of Classification Search
None
See application file for complete search history.

(56) References Cited

U.S. PATENT DOCUMENTS

| 8,815,178 B2 | 8/2014 | Bishop et al. |
| 9,532,747 B2 | 1/2017 | LaBelle et al. |

(Continued)

FOREIGN PATENT DOCUMENTS

| WO | 2007069111 A2 | 6/2007 |
| WO | 2007112527 A2 | 10/2007 |

(Continued)

OTHER PUBLICATIONS

International Search Report and Written Opinion dated Apr. 29, 2019 for corresponding PCT Application No. PCT/US2019/015209.
(Continued)

*Primary Examiner* — Kaylee R Wilson
*Assistant Examiner* — Jay B Shah
(74) *Attorney, Agent, or Firm* — Troutman Pepper Hamilton Sanders LLP

(57) ABSTRACT

A respiratory monitor, systems of respiratory monitoring, and methods of calibrating sensing equipment are described. The respiratory monitor may be configured to identify respiratory patterns while ignoring normal noise aberrations from a sensing device. The monitor may be configured for more comfortable use by a patient. Calibration techniques are also described. These calibration techniques may be employed to adjust sensing systems and to correct for unwanted noise in output signals of sensing equipment.

12 Claims, 21 Drawing Sheets

(52) U.S. Cl.
CPC .......... *A61B 5/6823* (2013.01); *A61B 5/6832* (2013.01); *A61B 5/7203* (2013.01); *A61B 5/742* (2013.01); *A61B 2560/0223* (2013.01); *A61B 2562/0233* (2013.01)

(56) References Cited

U.S. PATENT DOCUMENTS

| | | | |
|---|---|---|---|
| 9,909,942 | B2 | 3/2018 | LaBelle et al. |
| 10,386,321 | B2 | 8/2019 | LaBelle et al. |
| 2012/0289817 | A1 | 11/2012 | Rey et al. |
| 2014/0306894 | A1 | 10/2014 | Lee et al. |
| 2015/0057513 | A1 | 2/2015 | LaBelle et al. |
| 2015/0268108 | A1 | 9/2015 | LaBelle et al. |
| 2015/0305674 | A1* | 10/2015 | McPherson .......... A61B 5/4875 600/301 |
| 2016/0213287 | A1 | 7/2016 | Kuller |
| 2017/0055910 | A1* | 3/2017 | Kim ................. A61B 5/7203 |
| 2017/0202691 | A1 | 7/2017 | LaBelle et al. |
| 2019/0369042 | A1 | 12/2019 | LaBelle et al. |
| 2020/0064297 | A1 | 2/2020 | Probst et al. |
| 2020/0276030 | A1 | 9/2020 | LaBelle et al. |

FOREIGN PATENT DOCUMENTS

| | | |
|---|---|---|
| WO | 2010111484 A1 | 9/2010 |
| WO | 2013172929 A1 | 11/2013 |
| WO | 2014022586 A1 | 2/2014 |
| WO | 2014052470 A1 | 4/2014 |
| WO | 2015183893 A1 | 12/2015 |
| WO | 2016014572 A1 | 1/2016 |
| WO | 2016025153 A1 | 2/2016 |
| WO | 2018175448 A1 | 9/2018 |

OTHER PUBLICATIONS

Al-Khalidi, F. et al., "Respiration Rate Monitoring Methods: A Review", Pediatric Pulmonology, Jan. 2011, vol. 46, No. 6, pp. 523-529 <DOI:10.1002/ppul.21416>.

Al-Khalidi, F. et al., "Facial Tracking Method for Noncontact Respiration Rate Monitoring", 2010 7th International Symposium on Communication Systems, Networks & Digital Signal Processing (Newcastle upon Tyne, UK, Jul. 21-23, 2010), pp. 751-754 <DOI:10.1109/CSNDSP16145.2010.5580320>.

Aoki, H. et al., "Development of Non-restrictive Sensing System for Sleeping Person Using Fiber Grating Vision Sensor", MHS2001 Proceedings of 2001 International Symposium on Micromechatronics and Human Science (Nagoya, Japan, Sep. 9-12, 2001), 2001, pp. 155-160 <DOI:10.1109/MHS.2001.965238>.

Avago Technologies., "Optical Mouse Sensor: Data Sheet", Avago Technologies, May 2006, ADNS-5020, 24 pages <URL:http://forums.ni.com/attachments/ni/170/202305/1/ADNS>.

Borges, L. et al., "Smart-Clothing Wireless Flex Sensor Belt Network for Foetal Health Monitoring", 2009 3rd International Conference on Pervasive Computing Technologies for Healthcare (London, UK, Apr. 1-3, 2009), Aug. 2009, 4 pages <DOI:10.4108/ICST.PERVASIVEHEALTH2009.6028>.

Brady, S. et al., "Garment-Based Monitoring of Respiration Rate Using a Foam Pressure Sensor", 9th International Symposium on Wearable Computers (Osaka, Japan, Oct. 18-21, 2005), Dec. 2005, 2 pages <DOI:10.1109/ISWC.2005.23>.

Brooks, L. et al., "Assessment of Tidal Volume Over Time in PretermInfants Using Respiratory Inductance Plethysmography", Pediatric Pulmonology, Jun. 1997, vol. 23, No. 6, pp. 429-433 <DOI:10.1002/(SICI)1099-0496(199706)23:6<429::AID-PPUL6>3.0.CO;2-D>.

Corbishley, P. et al., "Breathing Detection: Towards a Miniaturized, Wearable, Battery-Operated Monitoring System", IEEE Transactions on Biomedical Engineering, Jan. 2008 (available online Dec. 2007), vol. 55, No. 1, pp. 196-204 <DOI:10.1109/TBME.2007.910679>.

Cretikos, M. et al., "The objective medical emergency team activation criteria: A case-control study", Resuscitation, Apr. 2007 (available online Jan. 2007), vol. 73, No. 1, pp. 62-72 <DOI:10.1016/j.resuscitation.2006.08.020>.

Ding, S. et al., "Derivation of Respiratory Signal from Single-Channel ECGs Based on Source Ding Statistics", International Journal of Bioelectromagnetism, 2004, vol. 6, No. 2, pp. 41-48.

Fieselmann, J. et al., "Respiratory Rate Predicts Cardiopulmonary Arrest for Internal Medicine Inpatients", Journal of General Internal Medicine, Jul. 1993, vol. 8, pp. 354-360 <DOI:10.1007/BF02600071>.

Folke, M. et al., "Comparative Provocation Test of Respiratory Monitoring Methods", Journal of Clinical Monitoring and Computing, Feb. 2002, vol. 17, No. 2, pp. 97-103 <DOI:10.1023/A:1016309913890>.

Folke, M. et al., "Critical review of non-invasive respiratory monitoring in medical care", Medical and Biological Engineering and Computing, Jul. 2003, vol. 41, pp. 377-383 <DOI:10.1007/BF02348078>.

Goldhill, D. et al., "A physiologically-based early warning score for ward patients: the association between score and outcome", Anaesthesia, Jun. 2005 (available online May 2005), vol. 60, No. 6, pp. 547-553 <DOI:10.1111/.1365-2044.2005.04186.x>.

Greneker, E., "Radar sensing of heartbeat and respiration at a distance with applications of the technology", Radar 97 (Edinburgh, UK, Oct. 14-16, 1997), 1997, pp. 150-154 <DOI:10.1049/cp:19971650>.

Hershenson, M. et al., "Changes in the Contribution of the Rib Cage to Tidal Breathing during Infancy", Rib Cage Contribution to Breathing in Infants, 1990, vol. 141, No. 4, pp. 922-925.

Hsu, C-H. et al., "Design and clinic monitoring of monitoring of a newly developed non-attached infant apnea monitor", Biomedical Engineering: Applications, Basis and Communications, Jun. 2005, vol. 17, No. 3, pp. 126-134 <DOI:10.4015/S1016237205000202>.

Johnson, A. et al., "Respiratory System", Biomedical Engineering Fundamentals, 2006, Ch. 7, pp. 7.1-7.17.

Kapel, F., "Convert Optical Mouse into Arduino Web Camera" [online], Frenki.net, Aug. 2017 [retrieved on Jan. 25, 2021 from archive.org, as it appeared on Aug. 8, 2017], retrieved from the internet: <URL:https://web.archive.org/web/20170808065247/http://www.frenki.net/frenkinet/2013/12/convert-optical-mouse-into-arduino-web-camera/>.

Kesner, S. et al., "Design Principles for Rapid Prototyping Forces Sensors Using 3-D Printing", IEEE/ASME Transactions on Mechatronics, Oct. 2011 (available online Jul. 2011), vol. 16, No. 5, pp. 866-870 <DOI:10.1109/TMECH.2011.2160353>.

Kundu, S. et al., "A Wearable Capacitive Sensor for Monitoring Human Respiratory Rate", Japanese Journal of Applied Physics, Apr. 2013, vol. 52, No. 4S, article 04CL05, 7 pages <DOI:10.7567/JJAP.52.04CL05>.

Lanata, A. et al., "Comparative Evaluation of Susceptibility to Motion Artifact in Different Wearable Systems for Monitoring Respiratory Rate", IEEE Transactions on Information Technology in Biomedicine, Mar. 2010 (available online Dec. 2009), vol. 14, No. 2, pp. 378-386 <DOI:10.1109/TITB.2009.2037614>.

Leonard, P. et al., "Standard pulse oximeters can be used to monitor respiratory rate", Emergency Medicine Journal, Nov. 2003, vol. 20, No. 6, pp. 524-525 <DOI:10.1136/emj.20.6.500-a>.

Mayer, O. et al., "Respiratory Inductance Plethysmography in Healthy 3- to 5-Year-Old Children", Chest, Nov. 2003, vol. 124, No. 5, pp. 1812-1819 <DOI:10.1378/chest.124.5.1812>.

Mazzanti, B. et al., "Validation of an ECG-Derived Respiration Monitoring Method", Computers in Cardiology (Thessaloniki Chalkidki, Greece, Sep. 21-24, 2003), May 2004, pp. 613-616 <DOI:10.1109/CIC.2003.1291230>.

Moody, G. et al., "Clinical Validation of the ECG-Derived Respiration (EDR) Technique", Computers in Cardiology, 1986, vol. 13, 7 pages.

Murthy, R. et al., "Touchless Monitoring of Breathing Function", The 26th Annual International Conference of the IEEE Engineering in Medicine and Biology Society (San Francisco, CA, Sep. 1-5, 2004), Mar. 2005, pp. 1196-1199 <DOI:10.1109/IEMBS.2004.1403382>.

(56) References Cited

OTHER PUBLICATIONS

Nakajima, K. et al., "Development of real-time image sequence analysis for evaluating posture change and respiratory rate of a subject in bed", Physiological Measurement, Mar. 2001, vol. 22, No. 3, pp. N21-N28 <DOI:10.1088/0967-3334/22/3/401>.

Nepal, K. et al., "Apnea Detection and Respiration Rate Estimation Through Parametric Modelling", Proceedings of the IEEE 28th Annual Northeast Bioengineering Conference (Philadelphia, PA, Apr. 21, 2002), Aug. 2002, pp. 277-278 <DOI:10.1109/NEBC.2002.999573>.

Nishigaki, Y. et al., "Development of new measurement system of thoracic excursion with biofeedback: reliability and validity", Journal of NeuroEngineering and Rehabilitation, May 2013, vol. 10, No. 45, 6 pages <DOI:10.1186/1743-0003-10-45>.

O'Brien, C. et al., "A comparison of algorithms for estimation of a respiratory signal from the surface electrocardiogram", Computers in Biology and Medicine, Mar. 2007 (available online Jun. 2006), vol. 37, No. 3, pp. 305-314 <DOI:10.1016/j.compbiomed.2006.02.002>.

Paradiso, R. et al., "A Wearable Health Care System Based on Knitted Integrated Sensors", IEEE Transactions on Information Technology in Biomedicine, Sep. 2005, vol. 9, No. 3, pp. 337-344 <DOI:10.1109/TITB.2005.854512>.

Prisk, K. et al., "Techniques for Measurement of Thoracoabdominal Asynchrony", Pediatric Pulmonology, Dec. 2002 (available online Nov. 2002), vol. 34, No. 6, pp. 462-472 <DOI:10.1002/ppul.10204>.

Reinvuo, T. et al., "Measurement of Respiratory Rate with High-Resolution Accelerometer and EMFit Pressure Sensor", Proceedings of the 2006 IEEE Sensors Applications Symposium (Houston, TX, Feb. 7-9, 2006), Jun. 2006, pp. 192-195 <DOI:10.1109/SAS.2006.1634270>.

Rovira, C. et al., "Integration of textile-based sensors and Shimmer for breathing rate and volume measurement", 5th International Conference on Pervasive Computing Technologies for Healthcare (PervasiveHealth) and Workshops (Dublin, Ireland, May 23-26, 2011), Oct. 2011, pp. 238-241.

Storck, K. et al., "Heat Transfer Evaluation of the Nasal Thermistor Technique", IEEE Transactions on Biomedical Engineering, Dec. 1996, vol. 43, No. 12, pp. 1187-1191 <DOI:10.1109/10.544342>.

Stromberg, N. et al., "Thoracoabdominal asynchrony in small children with lung disease—methodological aspects and the relationship to lung mechanics", Clinical Physiology, Oct. 1998, vol. 18, No. 5, pp. 447-456 <DOI:10.1046/.1365-2281.1998.00118.x>.

Subbe, C. et al., "Effect of introducing the Modified Early Warning score on clinical outcomes, cardio-pulmonary arrests and intensive care utilisation in acute medical admissions", Anaesthesia, Aug. 2003 (available online Jul. 2003), vol. 58, No. 8, pp. 797-802 <DOI:10.1046/j.1365-2044.2003.03258.x>.

Sweeney, K. et al., "Identification of Sleep Apnea Events using Discrete Wavelet Transform of Respiration, ECG and Accelerometer Signals", 2013 IEEE International Conference on Body Sensor Networks (Cambridge, MA, May 6-9, 2013), Aug. 2013, 6 pages <DOI:10.1109/BSN.2013.6575488>.

Tan, K. et al., "Real-Time Vision Based Respiration Monitoring System", 2010 7th International Symposium on Communication Systems, Networks & Digital Signal Processing (Newcastle upon Tyne, UK, Jul. 21-23, 2010), Sep. 2010, pp. 770-774 <DOI:10.1109/CSNDSP16145.2010.5580316>.

Tarassenko, L. et al., "Multi-sensor fusion for robust computation of breathing rate", Electronics Letters, Oct. 2002, vol. 38, No. 22, pp. 1314-1316 <DOI:10.1049/el:20020773>.

Tobin, M., "Respiratory Monitoring in the Intensive Care Unit", State of the Art: Respiratory Monitoring, 1988, vol. 138, pp. 1625-1642.

Torres, A. et al., "Assessment of Respiratory Muscle Effort Studying Diaphragm Movement Registered with Surface Sensors. Animal Model (dogs)", The 26th Annual International Conference of the IEEE Engineering in Medicine and Biology Society (San Francisco, CA, Sep. 1-5, 2004), pp. 3917-3920 <DOI:10.1109/IEMBS.2004.1404095>.

Werthammer, J. et al., "Apnea Monitoring by Acoustic Detection of Airflow", Pediatrics, Jan. 1983, vol. 71, No. 1, pp. 53-55.

Wertheim, D. et al., "Extracting respiratory data from pulse oximeter plethysmogram traces in newborn infants", Archives of Disease in Childhood Fetal & Neonatal Edition, 2009 (available online Nov. 2008), vol. 94, No. 4, pp. F301-F303 <DOI:10.1136/adc.2008.145342>.

Yu, S. et al., "Non-contact, Wavelet-based Measurement of Vital Signs using Thermal Imaging", ICGST International Journal of Graph Vision Image Process, 2006, vol. 6, pp. 25-30.

Zhang, X. et al., "Respiratory rate monitoring from the photoplethysmogram via sparse signal reconstruction", Physiological Measurement, Jun. 2016, vol. 37, No. 7, pp. 1105-1119 <DOI:10.1088/0967-3334/37/7/1105>.

Zhu, Z. et al., "Tracking Human Breath in Infrared Imaging", 5th IEEE Symposium on Bioinformatics and Bioengineering (Minneapolis, MN, Oct. 19-21, 2005), Dec. 2005, 5 pages <DOI:10.1109/BIBE.2005.55>.

\* cited by examiner

WEARABLE OPTICAL SENSOR FOR RESPIRATORY RATE MONITORING

CROSS-REFERENCE TO RELATED APPLICATIONS

This application is a U.S. National Stage filing under 35 U.S.C. § 371 of International PCT Application No. PCT/US2019/015209, filed Jan. 25, 2019, which claims priority to U.S. provisional application No. 62/622,500, filed Jan. 26, 2018, entitled "Wearable Optical Sensor for Respiratory Rate Monitoring," each of which is incorporated herein by reference in its entirety.

TECHNICAL FIELD

The disclosure relates to processes, articles of manufacture, devices, and systems involving biomedical monitoring, measurement, and analysis. More particularly, processes, articles of manufacture, devices, and systems involving respiratory measurement, monitoring, analysis, related functions, processes and/or systems are provided herein.

TECHNICAL BACKGROUND

Respiration rate is a vital sign that can provide insight into a subject's status and health progression. Respiratory rate may often be used to monitor the progression of illness where an abnormal respiratory rate may serve as a marker of serious illness. Respiratory rate may be employed as a high-certainty identifier of subjects at high risk. Respiratory rate may be more suitable than pulse and blood pressure to discriminate between stable subjects and subjects at risk. Various systems for measuring respiratory rate have been employed, but the form factor of these systems may provide difficulties to implement in a long-term monitoring setting, e.g., they are typically uncomfortable to wear and difficult to integrate with other technologies.

There have been different attempts and approaches to monitor respiratory rate. Different technologies that have been used to monitor respiratory rate may be approximated into two categories: contact and non-contact methods; see, e.g., Table 1; Al-Khalidi F, Saatchi R, Burke D, Elphick H, Tan S. Respiration rate monitoring methods: A review. Pediatric Pulmonology. 2011;46(6):523-529. In the contact-based category, some methods include the measurement of respiratory sound, airflow, chest and abdominal movement, transcutaneous $CO_2$, oxygen saturation, ECG derived, and capacitance. In the non-contact based methods there are radar-based, optical based, and thermal imaging. However, these measurement techniques can suffer from one or a combination of problems and, as such, they can have accuracy failings, can have reliability failings, and/or can be uncomfortable to wear. In particular, where devices are not comfortable to wear or are obtrusive and interfere with the activities during which respiration is intended to be monitored, subject compliance failure is likely.

TABLE 1

| Contact Based Methods | Noncontact Based Methods |
|---|---|
| Acoustic Methods | Radar Monitoring |
| Airflow Methods | Optical Based Methods |
| Chest and Abdominal Movements | Thermal Imaging Sensors |
| Transcutaneous $CO_2$ Monitoring | |
| $SpO_2$ Based Methods | |
| ECG Derived Methods | |

BRIEF SUMMARY

Embodiments relate to biomedical monitoring, measurement, and analysis of respiratory activity. This monitoring, measurement, and analysis may be undertaken with various devices, systems, and processes. These devices, systems, and processes may include the use of a physical chest monitor along with control devices and processes used to communicate with and interpret communications regarding the chest monitor. The interpretation may include applying filters and other data interpretation methodologies to discern between notable breathing events registered by the chest monitor and normal aberrations of movement registered by the chest monitor.

Embodiments may employ a chest monitor with an optical reader wherein the chest monitor may be mounted across or near the sternum of a subject or elsewhere and the movement may be registered by tracking movement between an optical reader and a grid of known spacing. This spacing on the grid may be preferably uniform but nonuniform grid spacing applications may also be applied provided that the non-uniform spacing of the grid is known. Nonuniform spacing may be advantageous at the perimeter of the grid to accommodate large movements at the beginning or end of a breathing cycle.

Embodiments may employ screening techniques to adjust for mechanical and electrical noise that may be created from the relative motion of the respiratory rate monitor components as well as environmental impacts. The various techniques that may be employed to decipher and interpret these signals can include filtering out ambient and unwanted noise on signals being carried from the sensor and being interpreted by microprocessors of embodiments. In so doing, embodiments may be better suited to decipher between respiratory activities and normal aberrations or other signal noise unrelated to respiratory activities.

Exemplary filtering and screening techniques can involve one or more microprocessors that may be configured: a) to filter mechanical noise by creating an average of a set of signals received from the optical sensor and subtracting this average from each subsequent signal received from the optical sensor for a subsequent predetermined period of time or cycles; b) to identify a difference in subsequent signals received from the optical sensor, add these identified differences to a container variable, and calculate an absolute displacement for a predetermined subsequent period of time or cycles; c) to identify an offset reduction by determining a running average for a received signal from the optical sensor and subtracting that running average from every subsequent signal received from the optical sensor for a predetermined subsequent period of time or cycles; d) to remove noise from a signal received from the optical sensor by averaging a predetermined number of samples and subtracting the average from every subsequent reading for a subsequent predetermined period of time or cycles; and e) to calculate the frequency of a waveform sensed by the optical sensor and determine peak lengths of each received waveform.

Equipment calibration techniques are also descried herein. These calibration techniques may be employed for purposes of calibrating an optical sensor or other system components. This calibration can include determining preferred oscillation frequencies, preferred operational distances, and preferred corrective algorithms.

Numerous embodiments are possible beyond those specifically described above and below. The embodiments described here are illustrative and should not be considered to be limiting. This includes that processes described herein may be undertaken in various orders unless a specific order is called for in the applicable claim or description. Moreover, fewer or more features or actions may accompany those specifically described herein. Likewise, disclosed embodiments, whether in the brief summary or detailed description may be further modified, including being altered using features and processes selected from different embodiments and using features and processes in different orders and configurations.

There are various adaptations of embodiments, and many permutations may be employed within the spirit and scope of this disclosure. Those of skill will understand that the invention is not to be limited to only those embodiments described herein and that other embodiments and applications consistent with the teachings herein would also fall with the scope of this disclosure. For example, and as explained in more detail below, these other permutations can include variations in timing of monitoring and analysis of chest monitor outputs, chest monitor configurations, chest monitor locations, and system communication techniques, as well as still other permutations.

DETAILED DESCRIPTION

Figure 1A:
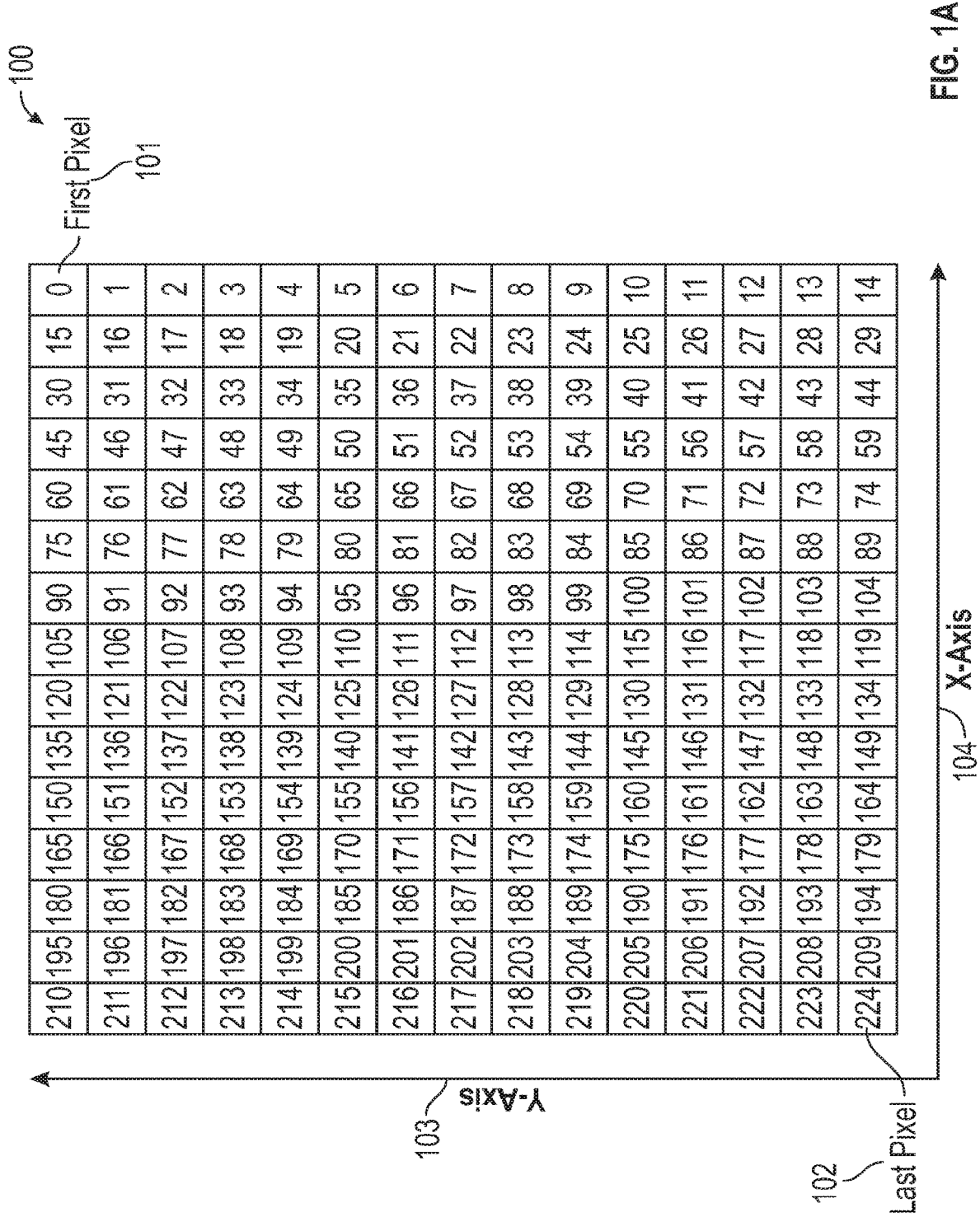
FIGS. 1A-1B show a reference grid along with an ADNS 5020 optical reader, as may be employed in embodiments.

Various approaches to respiratory rate monitoring based on a wearable sensor are provided. These approaches may be based on a combination of optical techniques and chest/abdominal movement measurement and may address the wearability aspect for continuous monitoring applications. In certain embodiments, the respiratory rate monitor may achieve similar or better reliability and accuracy of readings than those of the state of the art, while reducing the overall form factor. In certain embodiments, the provided respiratory rate monitor system and applicable features may be less obtrusive than existing technologies. In certain embodiments, the provided respiratory rate monitor system or related features may be comfortable, wearable, reliable, and accurate. Applications for the provided respiratory rate monitor system or its features may include sports, fitness, military, law enforcement, monitoring correlation of respiratory rates to hospital readmission rates, or otherwise monitoring subjects. Applications for the provided respiratory rate monitor system or its features may include human and veterinary applications.

In certain embodiments, the new respiratory rate monitor may comprise two tab attachment points capable of being attached to a subject's chest or abdomen. The tab attachment points may be attached to the anterior or posterior of a subject's chest or abdomen. This attachment may be directly to the skin of a subject as well as to garments worn by a subject. Preferably, the attachments are made directly to the skin of a subject. The tab attachment points may be attached using securements. The securements may include substances and methods suitable for attachment of medical sensors and devices, such as medical grade prosthetic adhesive and medical grade electrode adhesive. The tab attachment points may be attached to the chest or abdomen at an initial known distance apart from one another. The initial known distance may be the minimum distance needed for the respiratory rate monitor to register movement of the chest or abdomen. The initial known distance may be larger than the minimum distance needed for the respiratory rate monitor to register and/or measure movement of the chest or abdomen. The movement of the chest or abdomen registered and/or measured may be expansion, contraction, or both. The initial known distance may vary based on the size of the subject. The initial known distance may be approximately 2 to 40 inches, 3 to 10 inches, 3 to 5 inches, 3 to 15 inches, or 4 to 30 inches. In embodiments, the length of the tab may not affect the performance of the device. This may be because the optical sensor may only calculate the displacement of the surface beneath it, and the length of the slidable tab may therefore have no effect on calculations.

In certain embodiments, the tab attachment points may be capable of moving toward or away from each other as the chest or abdomen moves. The tab attachment points may be connected by a slidable tab that may be part of or fixedly attached or affixed to a first tab attachment point and slidably connected to a second tab attachment point. The connection may be via containment, i.e., the slidable tab may be contained in or by the second tab attachment point. The slidable tab may be constructed integrally with the first tab attachment point or may be permanently or removably affixed to it by any suitable means such as adhesive, Velcro, screws, rivets, or tabs. The second tab attachment point may comprise a means for slidably containing the slidable tab. The means for slidably containing the slidable tab may comprise a channel, v-grooves, a C-channel, a ball bearing like assembly, or the like. The channel or other means may restrict the slidable tab's movement. The channel or other means may restrict the slidable tab's movement such that it moves primarily along the axis of the slidable tab between the two attachment points. In other words, as the slidable tab moves in and out of an attachment point, the slidable tab and attachment point interface is constructed such that only two-dimensional movement occurs between the slidable tab and the attachment point. This two-dimensional movement, e.g., along an x-axis and a y-axis, may be read using a two-dimensional grid and an optical source and sensor. By reducing movement or eliminating movement in the z-axis between the sensor and the slidable tab, embodiments may be better suited to analyze and understand the respiratory patterns of a wearer.

In certain embodiments each tab attachment point may be constructed of flexible materials such as latex, silicon, or rubber; hard materials such a HDPE, delrin, HIPS, PVC, mylar; or a combination thereof. The channel or other means, for slidably containing the slidable tab, may form an integral part of a tab attachment point, or may be permanently or removably attached thereto. The channel or other means for slidably containing the slidable tab may likewise be constructed of flexible materials such as latex, silicon, or rubber; hard materials such a HDPE, delrin, HIPS, PVC, mylar; or a combination thereof. The slidable tab may also be constructed of flexible materials such as latex, silicon, or rubber; hard materials such a HDPE, delrin, HIPS, PVC, mylar; or a combination thereof. However, when these materials are selected it is preferable to maintain a connection interface between the slidable tab and the second attachment point that enables in-axis monitoring, i.e. little or no z-axis relative movement.

Each of the slidable tab, channel or other means for slidably containing the slidable tab, and each tab attachment point may be constructed by any suitable method, such as 3D printing, injection molding, laser cutting, or combinations thereof. The slidable tab, channel or other means for slidably containing the slidable tab, or both may have a smooth surface, be covered with a smooth layer, or both. The smooth surface and/or layer may reduce friction between the slidable tab and channel or other means for slidably containing the slidable tab. The slidable tab, channel or other means for slidably containing the slidable tab, or both may be constructed in a manner and using materials, coatings, or both that reduce friction. Such materials or coatings may include hydrophilic sprays, laminates, epoxies, resins, and the like.

In certain embodiments, the respiratory rate monitor may comprise an optical or laser sensing system. A sensor capable of sensing movement may be housed in one of the tab attachment points. In certain embodiments, the sensor may be housed in the tab attachment point that slidably contains the tab. The sensor may be capable of measuring movement; the sensor and its supporting electronic components may be capable of recording such measurements, storing such measurements, transmitting such measurements, or some combination thereof. As used herein, the term "house" or "housed" may refer to a first component being integrally constructed with a second component or removably or permanently attached to a second component; the terms may refer to a second component being partially or entirely covered by or enclosed within a first component, or to a second component being mounted to or on a first component such that the first component does not partially or entirely cover or enclose the second component.

In operation, respiratory rate may be mechanically read via the relative movement between the slidable tab and the tab attachment point slidably containing slidable tab (which may also house the sensor housing). This movement may be read as both attachment points are each secured to the chest of a subject, and the heaving of the subject's chest during respiration causes relative motion between the two secured components. This relative motion may be read by an optical sensor, such as a laser or LED and grid combination whereby output signals for each respiratory cycle are created. These signals may be read and analyzed for purposes of understanding a subject's respiratory state as well as for other reasons. These output signals may be on the order of millivolts or microvolts as well as other orders of magnitude.

Mechanical and electrical noise in addition to output signals may be created from the relative motion of the respiratory rate monitor components as well as environmental impacts. Various techniques may be employed to decipher and interpret these signals, including filtering out ambient and unwanted noise on signals being carried from the sensor and being interpreted by microprocessors of embodiments.

In embodiments, the tab attachment point housing the sensor may be constructed to accommodate the mounting of a lens or optical window, a light source, and a sensor. A planar substrate, with an optical window or lens may allow for a mechanical ground or fixation point for a light source (such as an LED) and a sensor to be attached. The sensor and light source may be optically connected via opposing ends of a window or lens, both pointing down through the window or lens to a surface, which may be the body of the wearer, the slidable tab, or a reference grid mounted to the body of the wearer or to the slidable tab.

In embodiments, the optical window may be constructed of any suitable transparent or translucent material, or may simply comprise an opening. In embodiments, a reference grid may be mounted or printed on the slidable tab, such that movement of the grid on the slidable tab may be sensed by the sensor. The lines of the grid may facilitate the sensing of movement by the sensor. These lines may be uniformly spaced as well as nonuniformly spaced to accommodate nonlinear movement or logarithmic ranges or for other reasons as well. The grid may move as the slidable tab moves in accordance with movement, such as respiration, of the wearer. The grid may be fabricated of any suitable material, such as plastic, paper, ceramic, and metal. The grid may be mounted or printed on the entirety of the slidable tab or on only a portion of the slidable tab, such as the portion that slides underneath the sensor when the respiratory rate monitor is in operation. The grid may be mounted or printed on both faces of the slidable tab, or only on the face of the slidable tab that faces the sensor.

In certain embodiments, other electrical components required or useful for the functioning of the sensor may also be housed in one of the tab attachment points. Other electrical components required or useful for the functioning of the sensor may also be housed in same tab attachment point that houses the sensor. For example, the tab attachment point may house components that perform any or all of the functions of data collection, data storage, data processing, and display of raw or processed data. Thus, the tab attachment point may house any or all of one or more power source, one or more sensor, one or more light source such as an LED, one or more lens or optical window, one or more capacitor, one or more resistance element, one or more data processing unit such as a microprocessor, software and/or one or more algorithm, one or more data storage unit, one or more unit configured to display raw and/or processed data, and the electrical connections necessary for connecting them.

In certain embodiments, the sensor and light source and the electrical and mechanical components used or required to collect movement data and transmit it may be housed in the tab attachment point along with various capacitors and other circuit components, such as microprocessors and storage. For example, any or all of the following may be found in sensor circuit embodiments: one or more power source, one or more sensor, one or more one or more light source such as an LED, one or more lens or optical window, one or more capacitor, one or more resistance element, one or more transmitter or other wireless communication unit configured to transmit and/or receive data, such as a Bluetooth module, and the electrical connections necessary for connecting them. Also, any or all of one or more power source, one or more data processing unit such as a microprocessor, software and/or one or more algorithm, one or more data storage unit, and one or more wireless communication unit configured to receive and/or transmit data, such as a Bluetooth module may be housed in another location as well, such as a cellphone or other remote controller. Accordingly, certain functions and monitoring may be carried out away from the mounted sensor system. For example, a cell phone or other mobile controller may perform any or all of the functions of receiving data, processing it, and any or all of transmitting, storing, or displaying it. Likewise, a remote controller may perform limited functions of receiving and transmitting data.

In embodiments, any wireless communication may also or alternatively be performed by a wired connection. For example, the attachment point housing the sensor may comprise a port and associated software and/or hardware for wired connection to a remote controller or other appliance. The remote controller or other controller in embodiments may have a port and associated software and/or hardware for wired connection.

In embodiments, as noted above, the sensor may register position changes due to the variations in distance between a moving part and a transducer. In certain embodiments, the sensor may comprise an optical sensor or laser motion sensor. The sensor may sense displacement that happens across a camera vision. In certain embodiments, the optical sensor may comprise a CMOS sensor. The optical sensor may also comprise an optical mouse sensor. The optical mouse sensor may comprise or be based optical mouse sensor ADNS-5020. This specific model can be configured to 500 or 1000 counts per inch (cpi). The principle of operation is based on digital image correlation. This process consists of a comparison between two successive images. These images are presented as arrays of pixels that have varying intensities. The intensity variation is due to the natural imperfections of the surfaces that refract the light that is irradiated onto them and subsequently captured by the camera. The sensor processes the differences between sequential images and calculates a displacement delta for X and Y, respectively. These deltas are stored in two registers that can be accessed for further manipulation, i.e. controlling a computer's cursor.

The sensor may comprise or may be based on optical sensor ADNS 2620. In embodiments, the sensor may comprise a laser motion sensor, such as laser motion sensor such as ADNS9800. In certain embodiments, the electrical components useful or necessary for the functioning of the sensor may be determined by reverse engineering, by studying literature, or by a combination thereof. The sensor may be an ADNS-5020, and the components may be determined by reverse engineering the computer mouse circuit and studying other applications that have been used to access the pixel array in the ADNS-5020. The mechanism presented in Kesner S, Howe R. Design Principles for Rapid Prototyping Forces Sensors Using 3-D Printing. IEEE/ASME Transactions on Mechatronics. 2011;16(5):866-870, which is incorporated by reference in its entirety, may be used in embodiments.

Embodiments may include a) a stand-alone version that would require a microprocessor 5V DC output capabilities to power the sensor up, a communication unit such as a Bluetooth module to transfer data wirelessly and a battery to power the monitor up; and b) an add-on version where the monitor would have the means to connect to another unit that will provide power and communication capabilities through wired communication.

Process aspects of embodiments may include code written to control the behavior of the monitor. Examples of such code are provided below ("Arduino code") in this document.

As noted above, an optical mouse sensor AD5020 may be employed. This sensor is exemplary as it may be replaced by other types of optical sensor or by a laser sensor. In case that the sensor would be used as an add-on, only the light source (LED), and the optical sensor may be preferably required to remain in the device.

Mechanical noise may be filtered out by creating an average of a set number of samples and subtracting it from each subsequent sample. This enables the signal in certain preferred embodiments to remain around the x-axis and better reflect the respiration pattern. Electrical noise may not be a problem, since the sensor is based on the readings of its camera; as long as the electrical components are properly soldered and placed on the board, electrical noise should not meaningfully impact the readings.

In certain embodiments, to properly make sense out of the deltas calculated by the sensor, they may be added to a container variable to calculate absolute displacement. In addition, an offset reduction algorithm consisting of a running average subtracted from every sample may be implemented in the data acquisition interface.

In certain embodiments, the movement of the chest or abdomen may correlate with the respiratory rate of the wearer of of the respiratory rate monitor. The correlation may be improved by removing noise from the signal. Noise may be removed from the signal using various techniques described herein as well as others that are similar. In embodiments, noise may be removed from the signal by averaging a set number of samples and subtracting the average from every reading. The calibration may be performed against a grid on the moving platform, under the sensor and light source, to determine the value of each unit recorded by the sensor. If desired, the units for position may then be converted to millimeters, as explained further below. Given the principle of operation of the device, the same method of calibration may be used for all subjects.

In embodiments, the frequency and pattern observed from the displacement signal from the sensor may match the subject's breathing frequency and pattern. From the signal, it is possible to extract the breathing frequency by calculating the frequency of the waveform. Also, chest expansion may be obtained from the displacement values, as a longer peak would mean a greater chest expansion.

The subject whose respiration in measured or monitored in certain embodiments may be an animal where the animal may be a mammal, a reptile, or a bird. Still further, the animal may be a companion animal, an agricultural animal, a laboratory animal, a zoological animal, or a wild animal. Likewise, the animal may be a companion mammal, an agricultural mammal, a laboratory mammal, a zoological mammal, or a wild mammal. In certain embodiments, the animal may be a human. A subject may also be referred to as a "patient." A subject may also be referred to as a "wearer" or a "user". In certain embodiments, the subject may be embryonic or fetal, infant, juvenile or pediatric, adolescent, young adult, adult, or geriatric. In certain embodiments, the age of the subject may range from pre-birth to 100 or more years old. In certain embodiments, a subject may be male, female, androgynous, or inter-sexual of any ethnic origin.

In certain embodiments, the subject may be healthy. In certain embodiments, the subject may have a disease, may be at varying stages of a disease, and/or may be responding or not responding to treatment. In certain embodiments, the subject may have more than one disease; in such embodiments only one or more than one disease may be assessed.

Figure 1B:
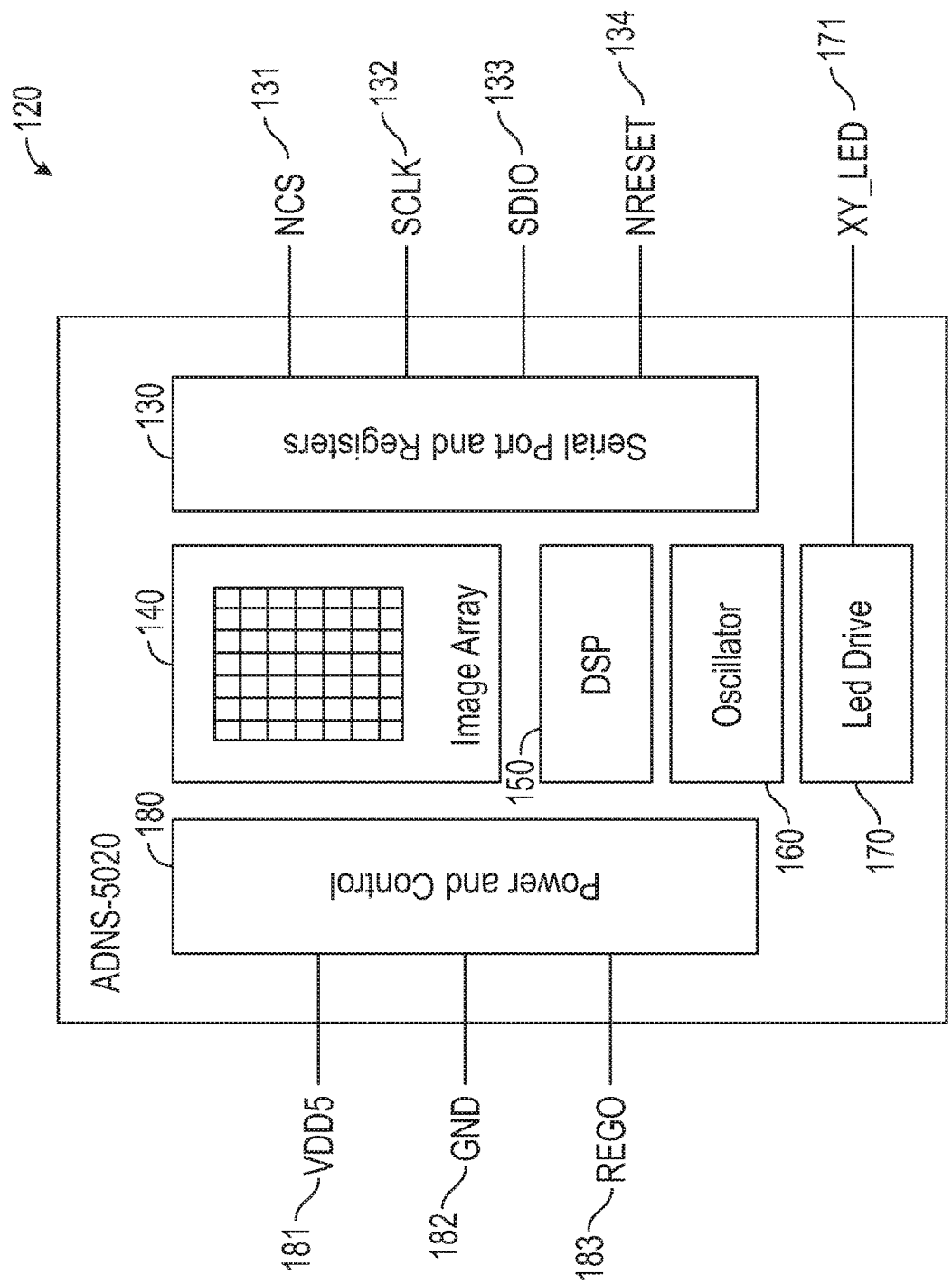

FIGS. 1A and 1B show an ADNS 5020 optical reader (FIG. 1B) along with a reference grid (FIG. 1A) as may be employed in embodiments. The reference grid 100 may be read by the optical reader 120 in certain embodiments. This reading may occur during calibration phases as well as during other operational phases, including normal operation. The reference grid 100 may include pixels, such as first pixel 101 and last pixel 102 arranged along x-axis 104 and y-axis 103. The optical reader 120 may include power and control modules 180, communication modules (such as serial port registers 130), onboard oscillators 160 for timing or other purposes, an LED drive 170 for creating optical outputs, a DSP (digital signal processor) 150 for processing digital signals, and a reference image array 140 for noting relative motion between components of an optical sensor system of embodiments. The optical reader 120 may include Serial Port and Registers 130 with inputs for Chip Select (active low input) (NCS) 130, Serial Clock Input (SCLK) 132, Serial Port Data Input and Output (SDIO) 133, and Reset Pin (active low input) (NRESET) 134. The optical reader may also include LED Control (XY_LED) 171, Supply Voltage (VDD5) 181, Ground (GND) 182, Oscillator 160, Digital Signal Processor 150, and Regulator Output (REGO) 183.

Figure 2A:
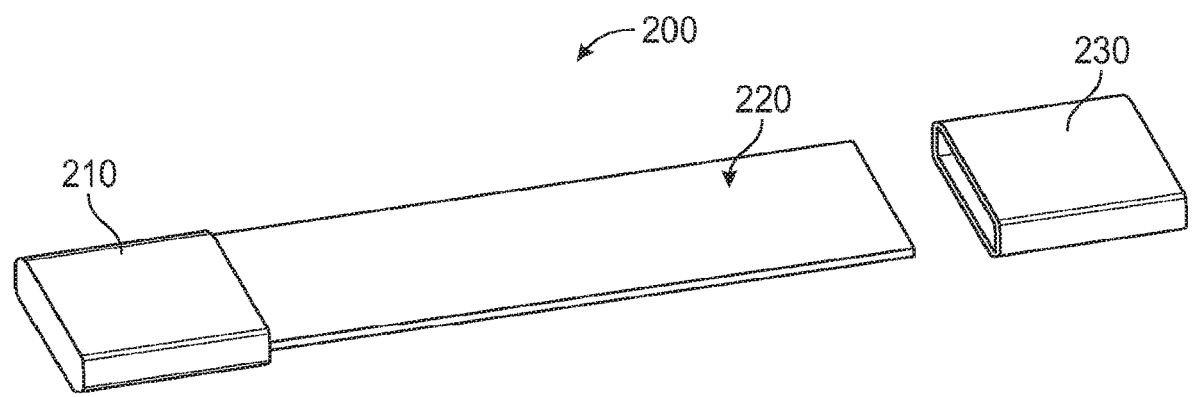
FIGS. 2A-2D show an optical sensing system and its placement directly on a subject's chest, as may be employed in embodiments.
Figure 2B:
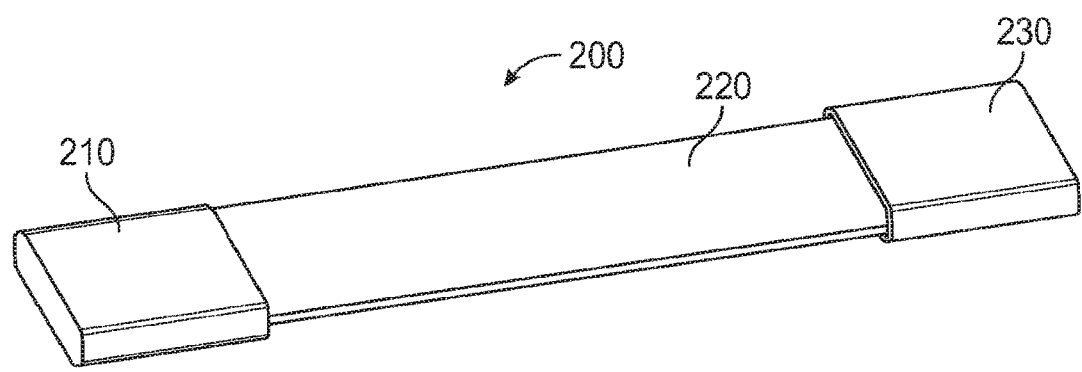
Figure 2C:
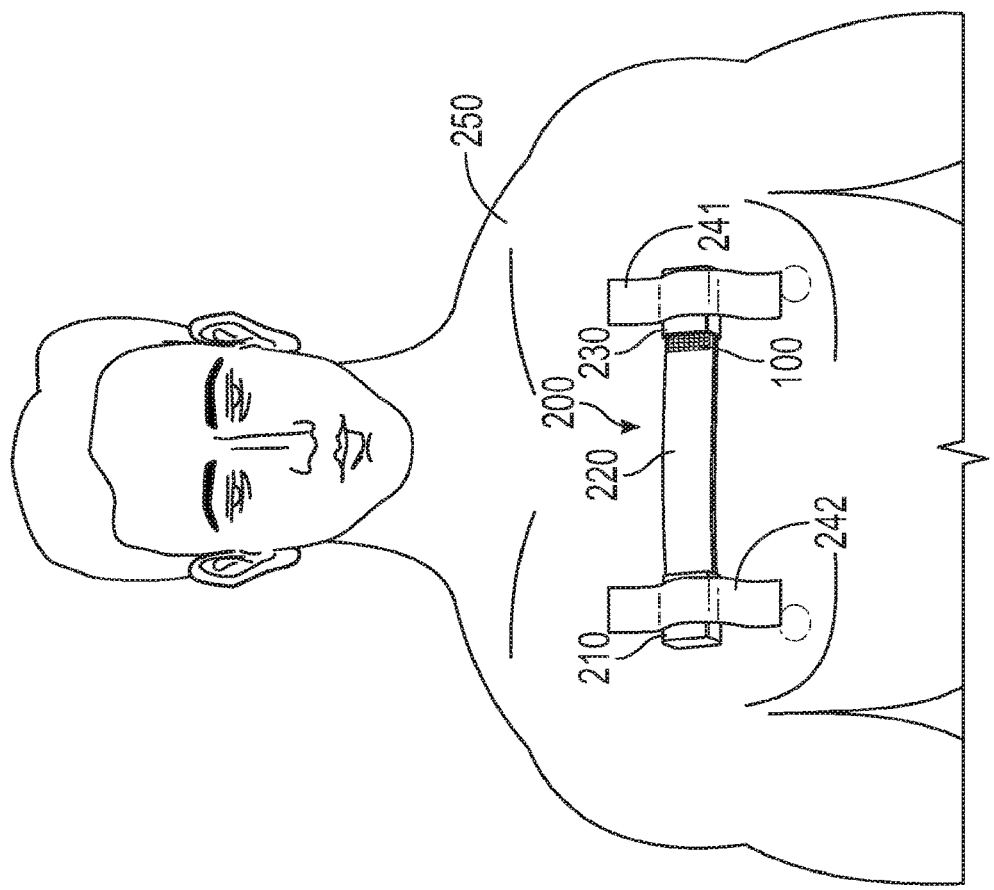
Figure 2D:
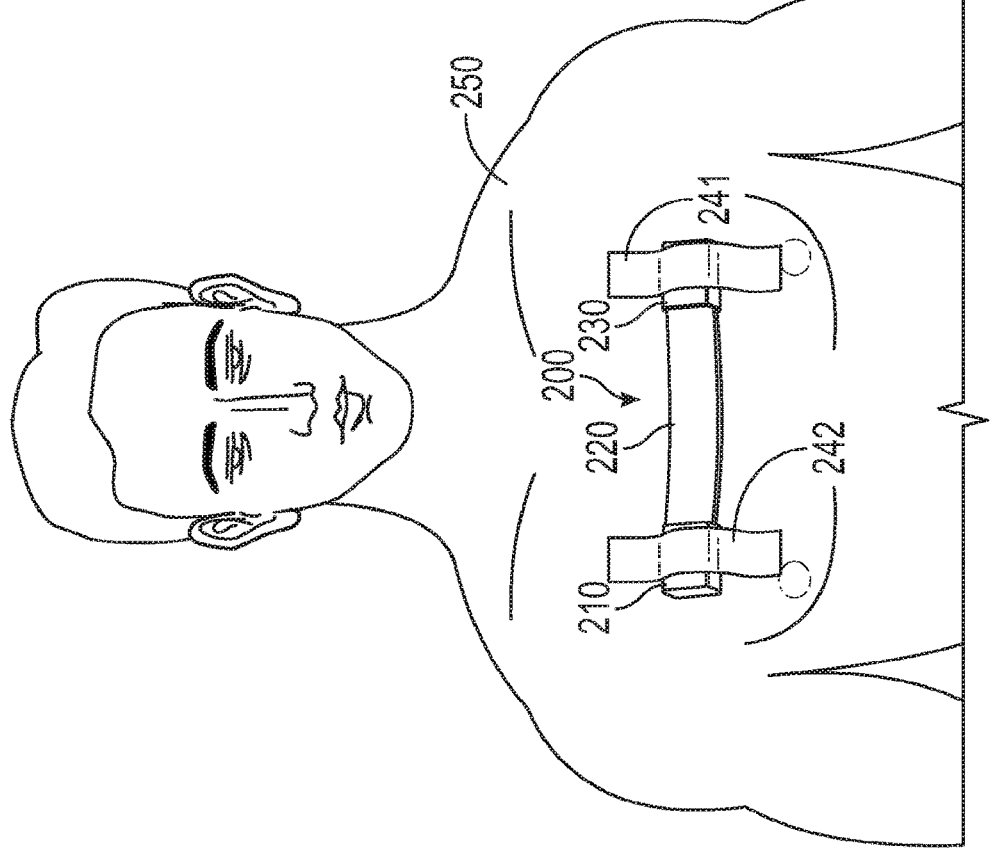

FIGS. 2A-2D show an optical sensing system 200 as may be employed in embodiments. FIG. 2A includes a basic structure of a first tab fixing or attachment point 210, a slidable tab 220, and a second tab fixing or attachment point 230, which may also serve as or house a sensor housing, as may be used in embodiments. FIG. 2A shows a slidable tab 220 attached to a first tab attachment point 210 and separated from the second tab attachment point 230. FIG. 2B shows the slidable tab 220 attached to the first tab attachment point (tab fixing point) 210 and slidably contained by the second tab attachment point 230. FIG. 2C and FIG. 2D show the optical sensing system 200 positioned on an exemplary subject's chest 250 and attached thereto by first and second securements 241, 242. FIG. 2C shows the subject's chest in a first position, which may correspond to exhalation, in which slidable tab 220 is in a first position. FIG. 2D shows the subject's chest in a second position, which may correspond to inhalation, in which slidable tab 220 is in a second position. In this second position, slidable tab 220 has slid and is in a changed position relative to second tab attachment point 230. This movement, or change in position, may be sensed and readable by a sensor (not shown) housed in second tab attachment point 230. The sensing and reading may be aided by grid 100.

Figure 3:
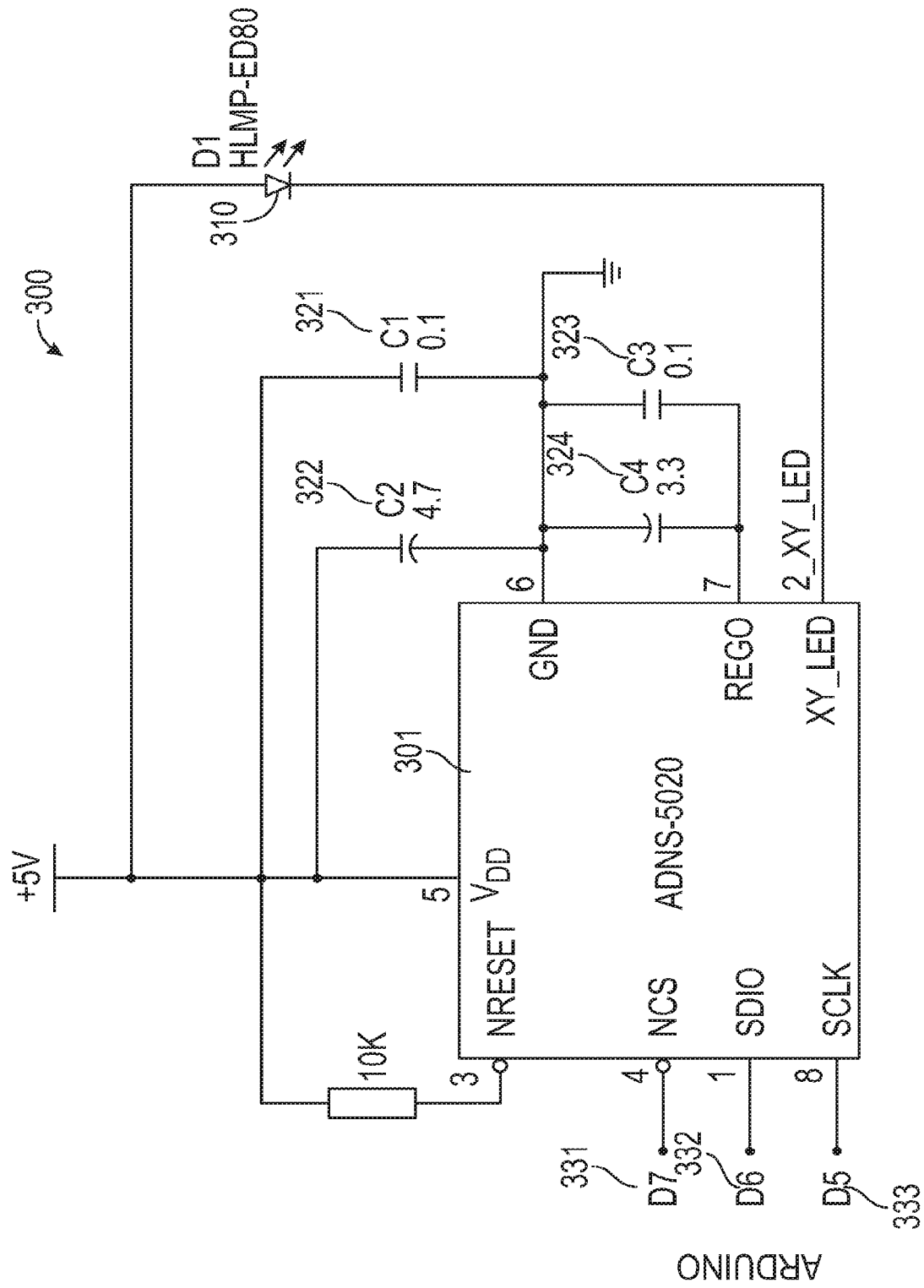
FIG. 3 shows circuit topology, including wiring for a microprocessor, as may be employed in embodiments.

FIG. 3 shows circuit topology, including wiring, for a microprocessor that may be employed in embodiments. FIG. 3 includes a circuit schematic 300, which may be useful for the supporting the output or operation of the sensor, in certain embodiments. Sensor ADNS-5020 301, which may be used in embodiments, is specifically labelled in the circuit along with various circuit components, such as LED 310, capacitors 321, 322, 323, and 324, and inputs 331, 332, and 333.

Figure 4A:
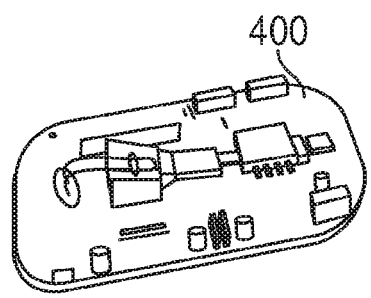
FIGS. 4A-4C show a respiratory rate monitor and its placement directly on an exemplary subject's chest, as may be employed in embodiments.
Figure 4B:
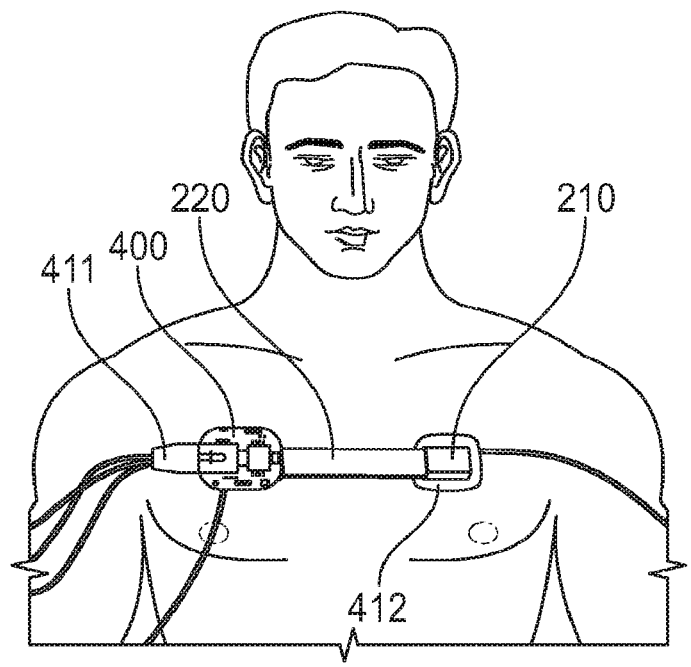
Figure 4C:
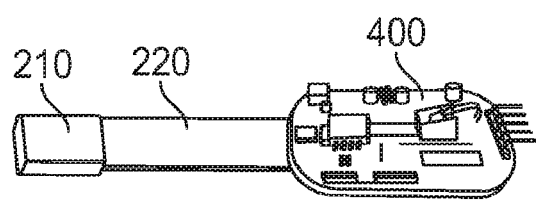

FIGS. 4A-4C show a respiratory rate monitor according to embodiments, and its placement directly on an exemplary subject's chest. FIG. 4A shows a sensor apparatus 400. FIG. 4B shows a sensor apparatus 400 attached to a second tab attachment point (not shown) that slidably houses a slidable tab 220, which slidable tab is non-movably attached to a first tab attachment point 210; FIG. 4C shows a sensor 400, first tab attachment point 210, and slidable tab 220 that may be used in embodiments. Clinical grade electrodes 411 and 412 are also shown in FIG. 4B.

Figure 5:
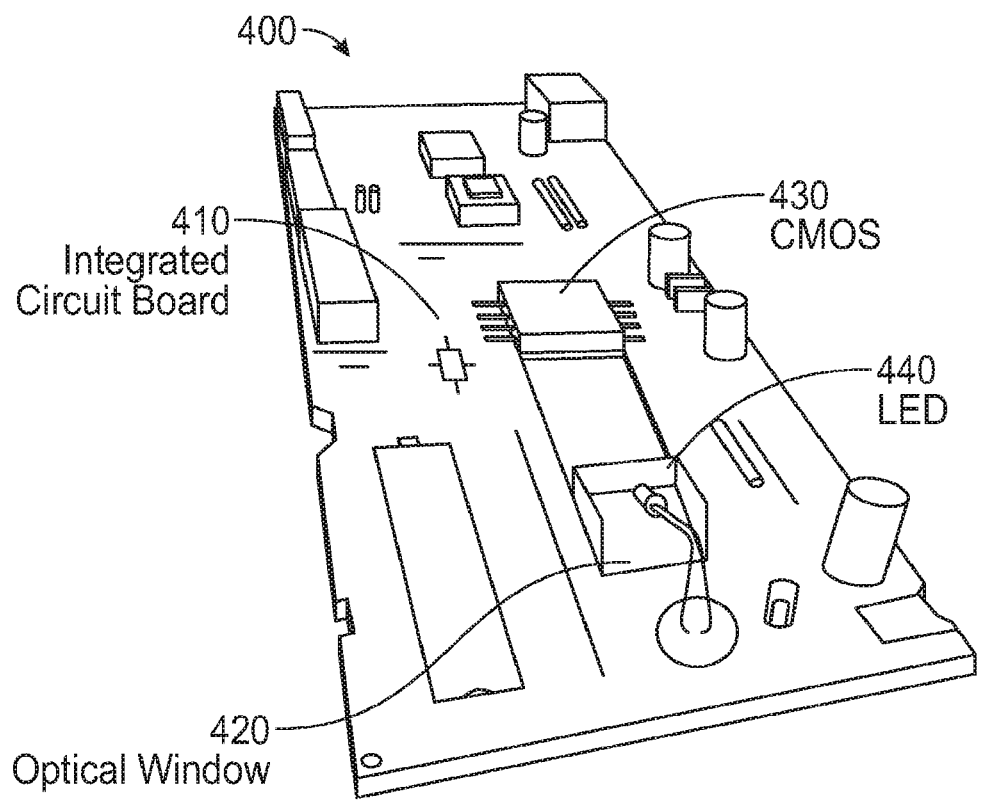
FIG. 5 shows a circuit board employing an optical window, CMOS memory, and LED, as may be employed in embodiments.

FIG. 5 shows sensor apparatus 400 comprising integrated circuit board 410, optical window 420, CMOS 430, and LED 440. The LED 440 is facing downwards through the optical window 420, light passes thru the optical window 420 and is bounced off of the surface underneath, such as the slidable tab, a grid on the slidable tab, or the skin, and reflects into the CMOS 430 detector. Relative movement of the surface underneath is intended to be registered by the CMOS 430.

Thus, as noted above, embodiments may include a respiratory rate monitor comprising two attachment points capable of being attached to the outside of a subject's chest. These embodiments may be constructed such that attachment points are maintained at an initial fixed distance apart from one another when initially attached to the chest. The initial fixed distance is preferably the minimum distance needed for the respiratory rate monitor to register movement of the chest. Specifically, the distance is about 3 to 5 inches for a human subject.

The attachment points in embodiments are capable of moving toward or away from each other as the chest moves. The attachment points may be connected by a slidable tab that that is affixed to the first attachment point and slidably contained in the second attachment point, such as is illustrated in FIGS. 2A-2D and 4A-4C. The second attachment point comprises a channel, which slidably contains the tab. The channel may restrict the tab's movement so that it moves primarily in the axis of interest. These attachment points may be constructed of PVC sheet and the tab may be constructed of PVC sheet and be approximately 1-2 inches in length. Optical sensors in embodiments, which are capable of sensing movement, are preferably housed in the attachment point that slidably contains the tab, such as is illustrated in FIGS. 2A-2D and 4A-4C. As noted above, other electrical components required for the functioning of the sensor may also be housed in the same attachment point that houses the sensor. Sensors of embodiments may be variations of an optical mouse sensor (ADNS-5020). This specific model can be configured to 500 or 1000 counts per inch (cpi). As noted above, the principle of operation may be based on digital image correlation, which is a process consisting of a comparison between two successive images. These images are presented as arrays of pixels that have varying intensities. The intensity variation is due to the natural imperfections of the surfaces that refract the light that is irradiated onto them and subsequently captured by the camera. The sensor processes the differences between sequential images and calculates a displacement delta for X and Y, respectively. These deltas may be stored in two registers that can be accessed for further manipulation, i.e. controlling a computer's cursor. To properly analyze the deltas, embodiments may use a container variable to calculate absolute displacement. In addition, an offset reduction algorithm consisting of a running average subtracted from every sample may be implemented in the data acquisition interface.

Equipment Testing, Calibration, and Operation

Equipment may be tested and calibrated once selected for embodiments. This calibration, testing, and subsequent operation may involve various procedures and equipment to calibrate and test various aspects of embodiments. The calibration may be tailored to optical sensitivity, noise reduction, oscillation speed, and for other variables as well. Testing, calibration and subsequent operation may employ using various testing apparatus and techniques. These testing apparatus and techniques may include a moving platform and a servo motor and may employ Lego Mindstorms. Data acquisition system employed may use a combination of Arduino IDE, Python and MATLAB to automate plot generation. Various examples of calibration, testing, and subsequent operation, which may be employed in embodiments, follow.

For one, embodiments may be tested or calibrated by displacing the sensor a random distance within a range of 0 to 20 mm. Subsequently, the displacement may be measured using a digital caliper and a relationship may be established between the measured distance and the recorded units for subsequent operation. This calibration protocol may include approximately 15 second runs of periodic movements read and saved to a .txt file with their respective plots. The software employed may include Python Script readSerial; Arduino Script mouse_position; Lego Mindstorms-controlled testing apparatus; Lego Mindstorms software; MATLAB script plotExperimentsFolder; Stopwatch and the steps employed may include the following:
1. Determine combination of speed (power setting in Mindstorms software) and displacement (degrees—approximately 5 deg=2 mm) with an understanding that certain test motors may not be reliable at power settings less than 50.
2. Connect the mouse to the Arduino board with preloaded mouse_position file.
3. Open command line interface (CLI from this point forward) and go to the directory where the python script is.
4. Run tests: Making sure the mouse and the Arduino board are properly connected. (Run Serial Monitor (CTRL+SHIFT+m) in Arduino IDE to check this, enter r in the prompt area and press enter, and modify the python script to match the baud rate and the port that they are using.)
For each combination of tests:
4.1 Modify the settings for the motor in the Python script accordingly and upload the file. These settings would normally be
PORT in which the Arduino is connected and the BAUD rate.
4.2 Run the python script. The format for the run at CLI is "python readSerial.py "nameofthefile.txt""
4.3 At prompt one can use these options:
y for start test
n for exit script (the script exits automatically after the test is run)
4.4 When conducting calibrations it is preferable to press enter and start the stopwatch at the same time.
4.5 At the 1 second mark (approximately), press the Mindstorms button.
4.6 At the 14 second mark stop the program by pressing the dark gray button on the Mindstorms brick.
4.7 Wait for the script to display "Done!"
5. Copy the text files from the location where they were stored (same directory where the python script is) to the folder where they are desired to be stored.
6. Open MATLAB and run the MATLAB script. This script preferably will plot and save the figures in the same directory where the text files are.

Figure 6:
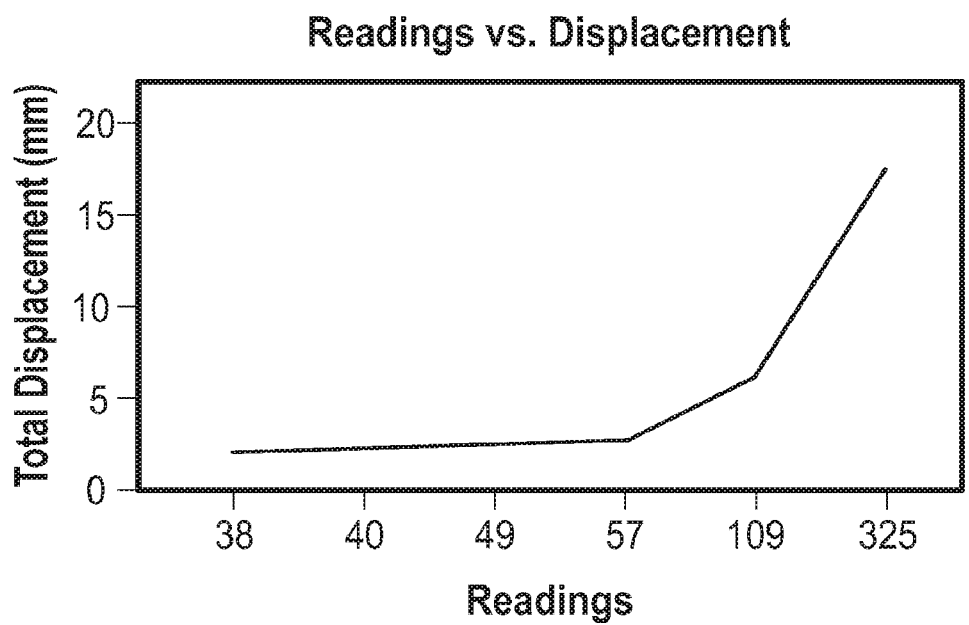
FIG. 6 shows the relationship between readings and displacements, as may be employed in embodiments.
Figure 7A:
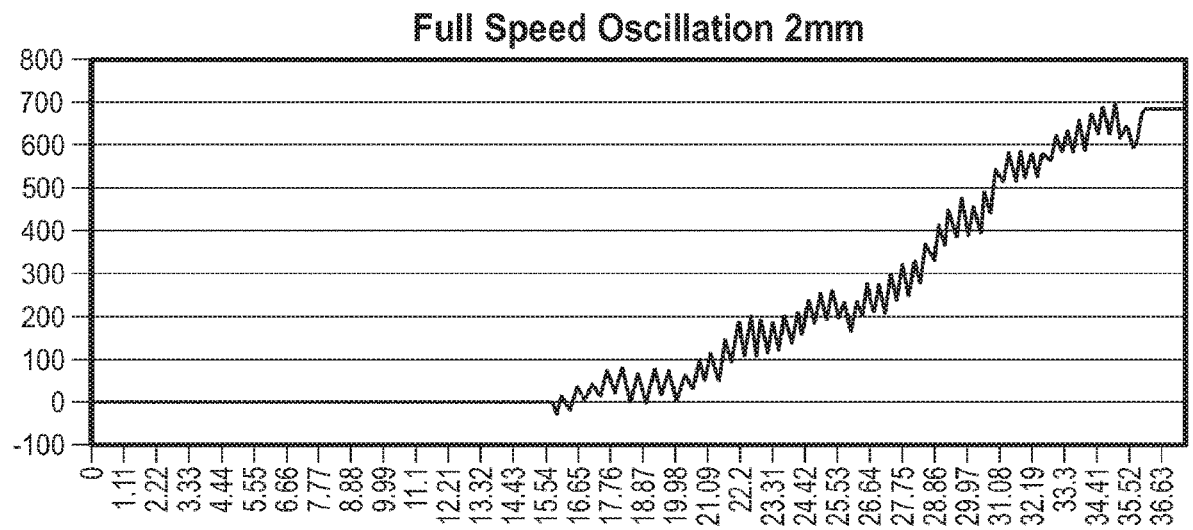
FIGS. 7A-7B show 2 mm displacement at full and half motor power, as may be employed in embodiments.
Figure 7B:
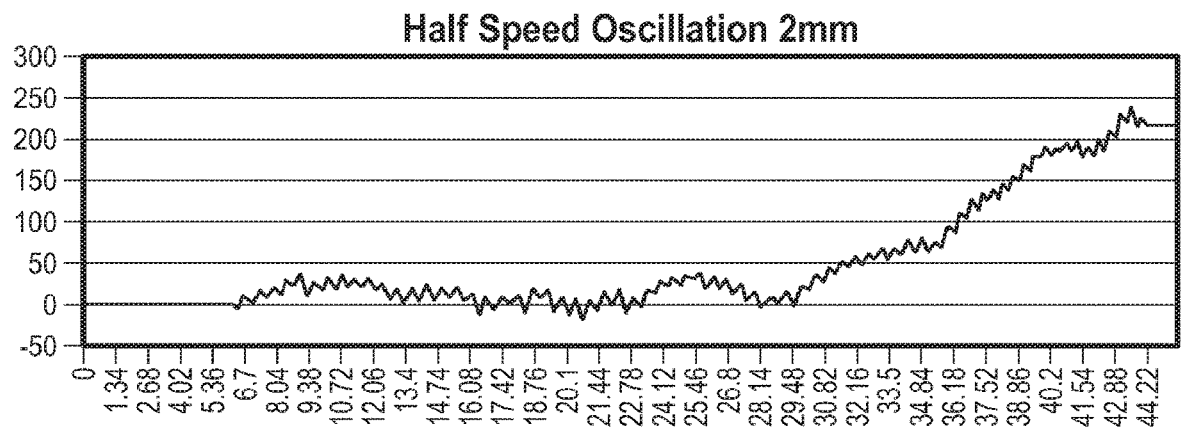
Figure 8A:
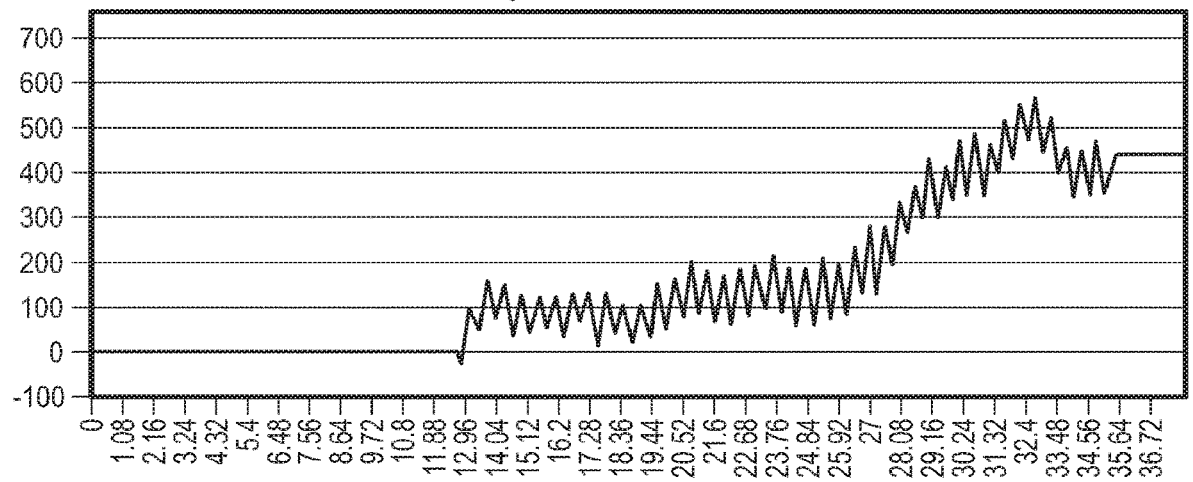
FIGS. 8A-8B show 4 mm displacement at full and half motor power, as may be employed in embodiments.
Figure 8B:
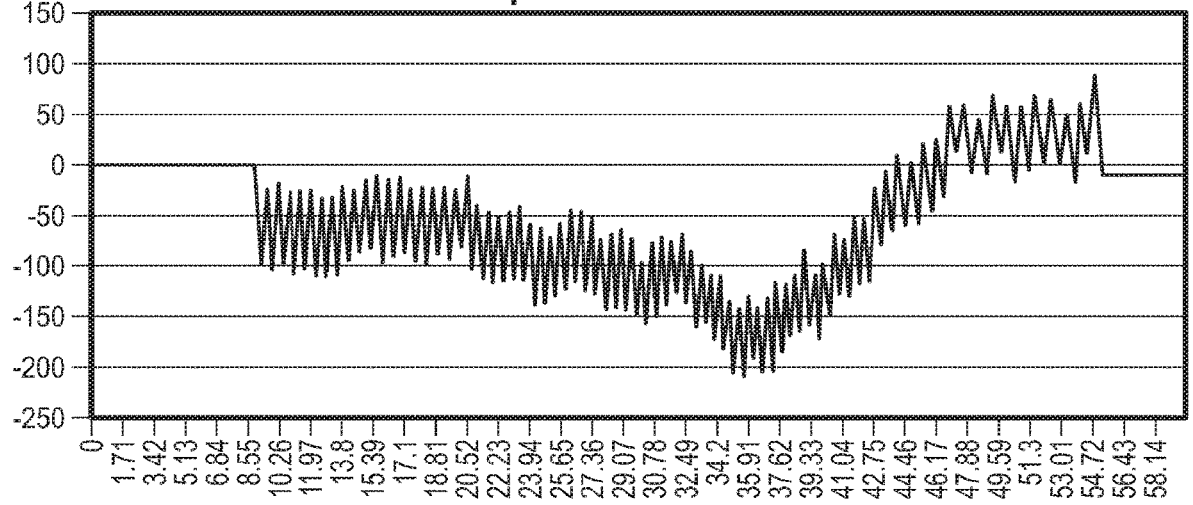
Figure 9A:
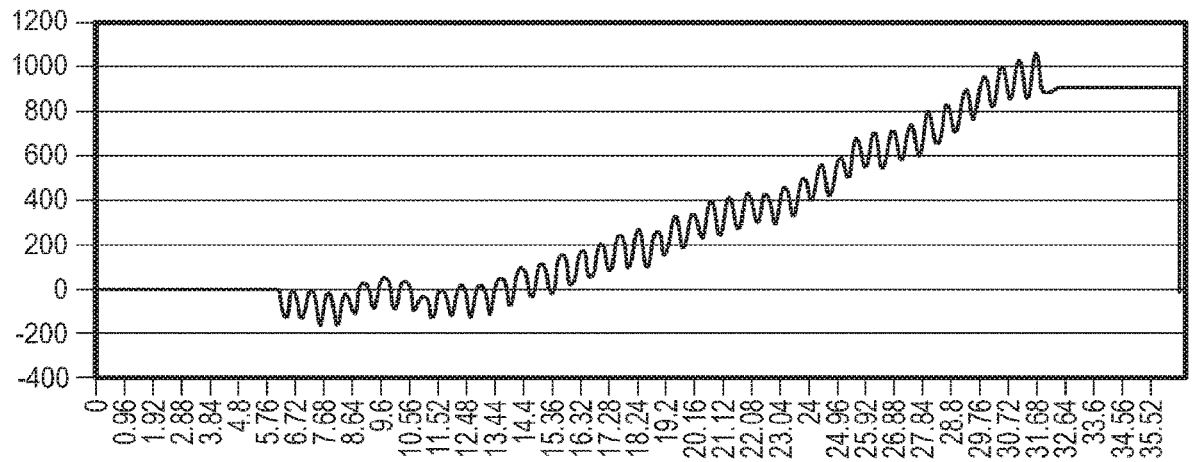
FIGS. 9A-9B show 8 mm displacement at full and half motor power, as may be employed in embodiments.
Figure 9B:
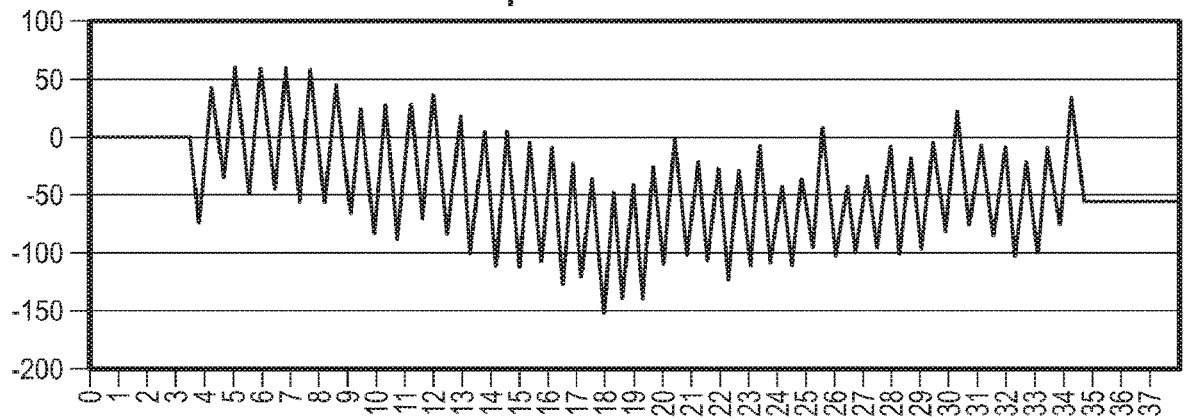
Figure 10A:
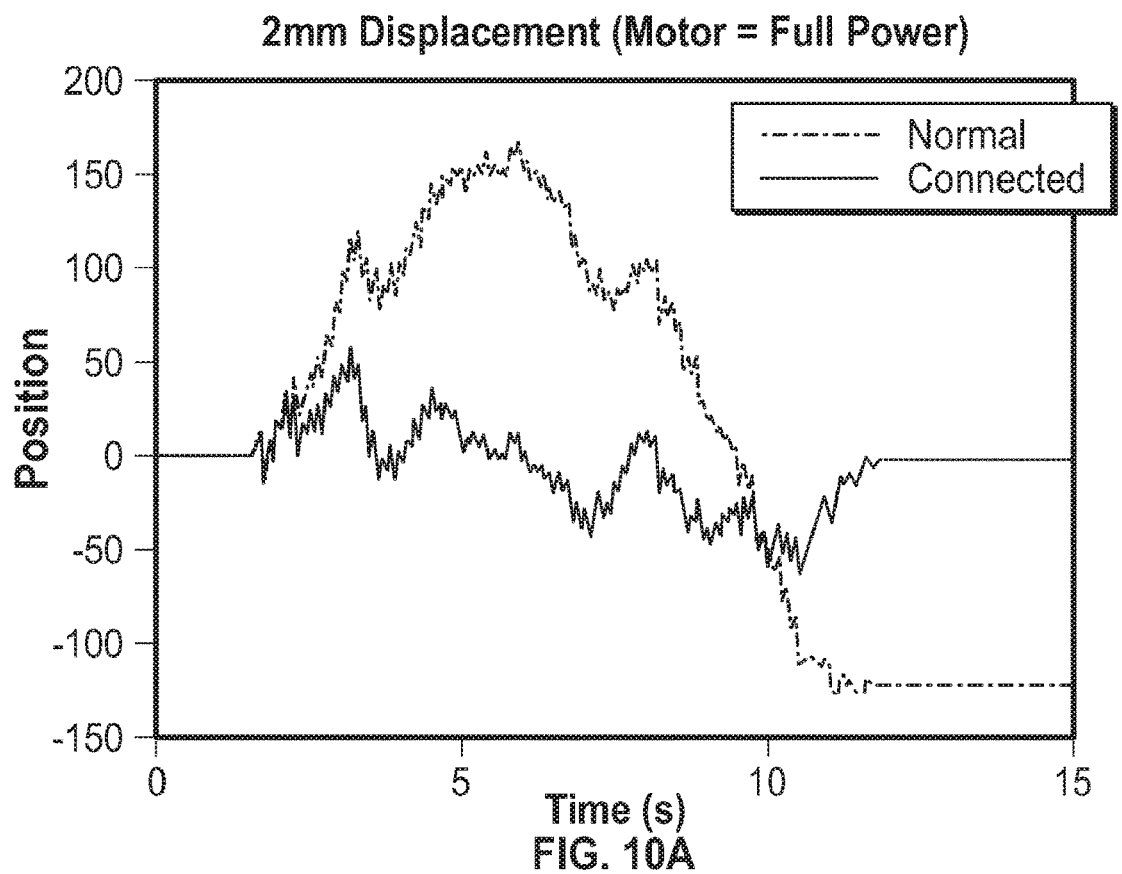
FIGS. 10A-10F show displacement versus time calibration readings being interpreted via an offset reduction algorithm, as may be employed in embodiments.
Figure 10B:
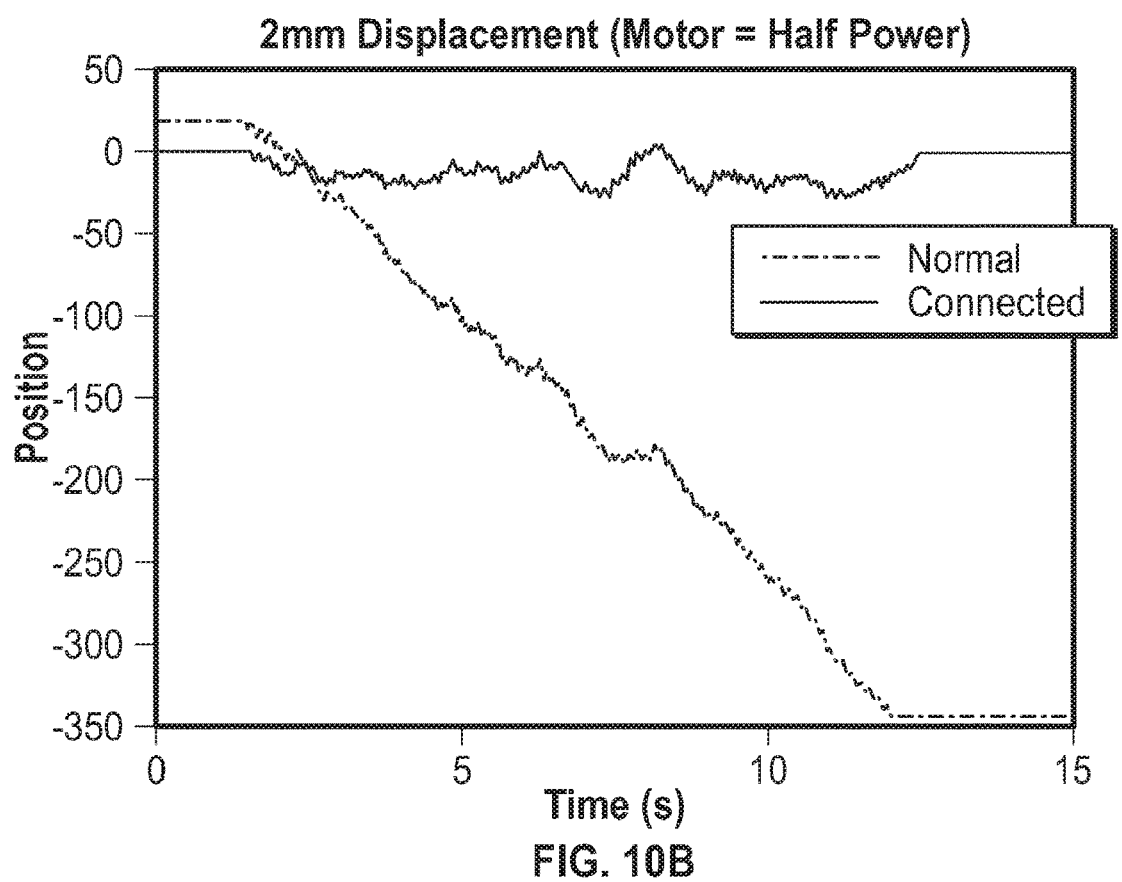
Figure 10C:
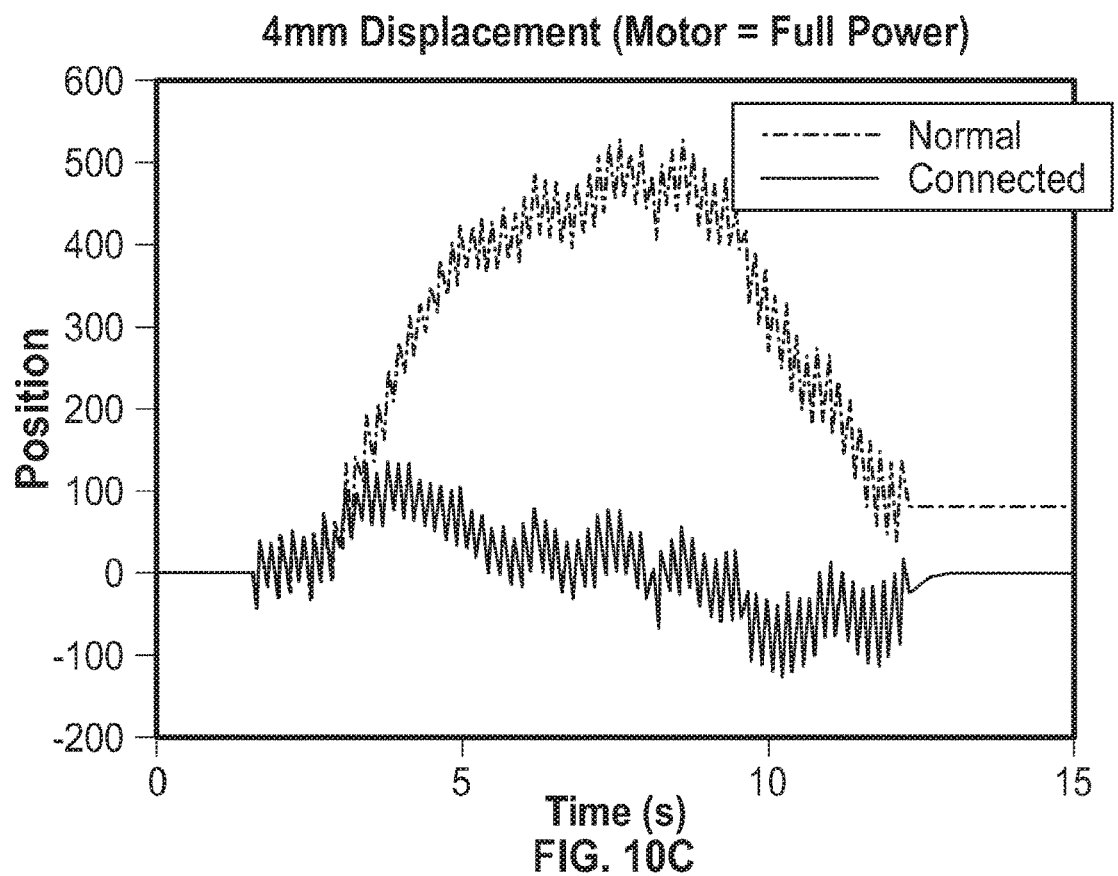
Figure 10D:
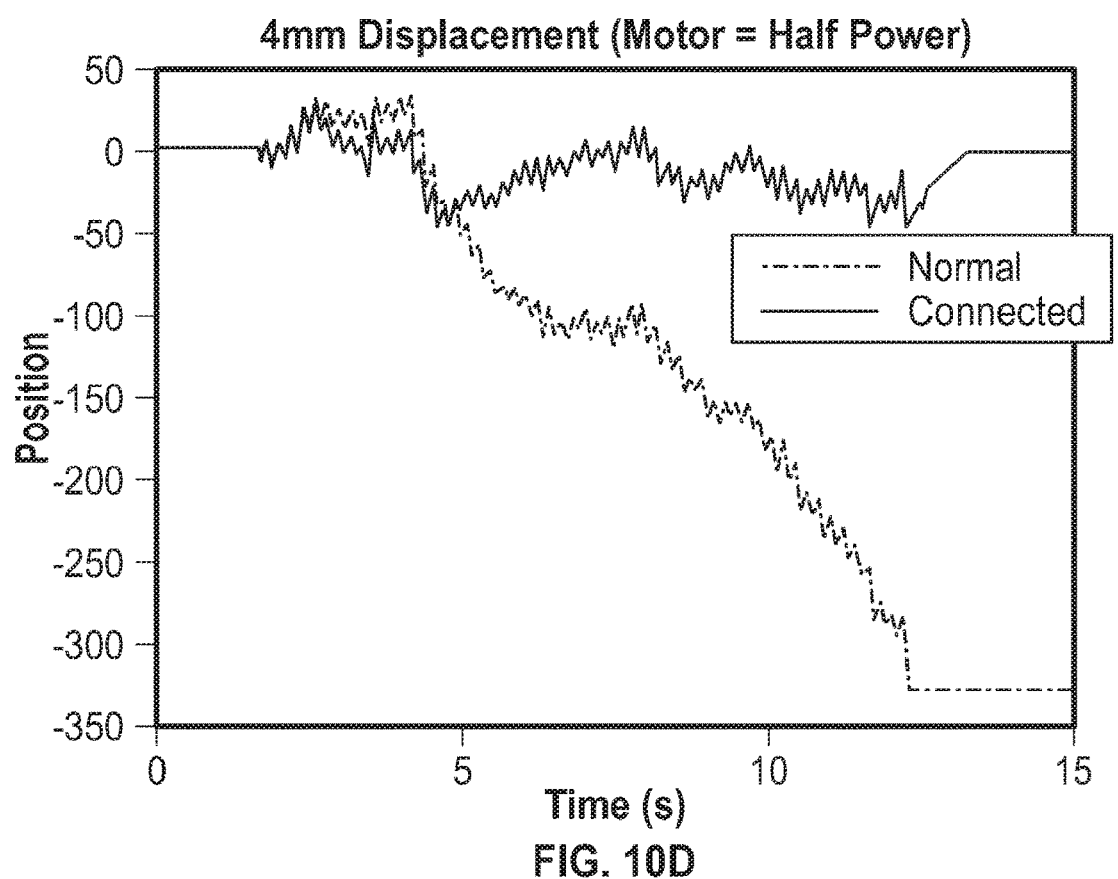
Figure 10E:
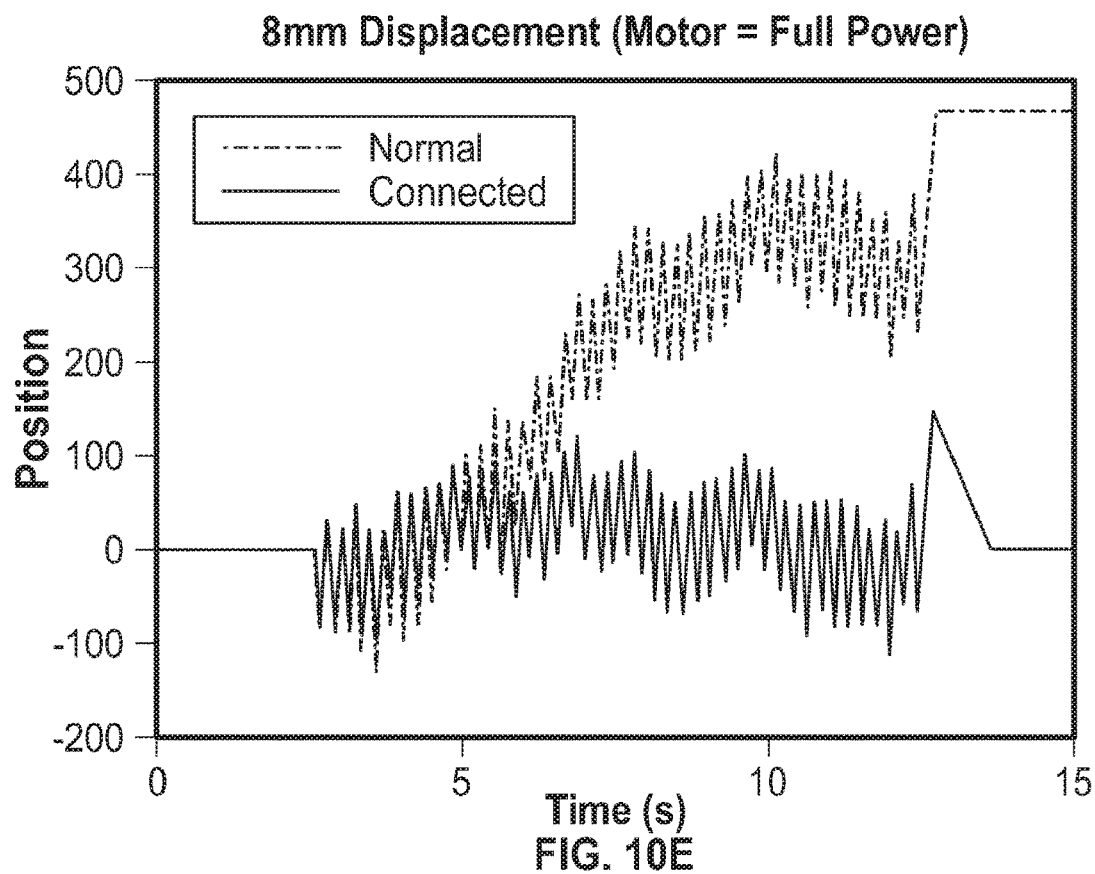
Figure 10F:
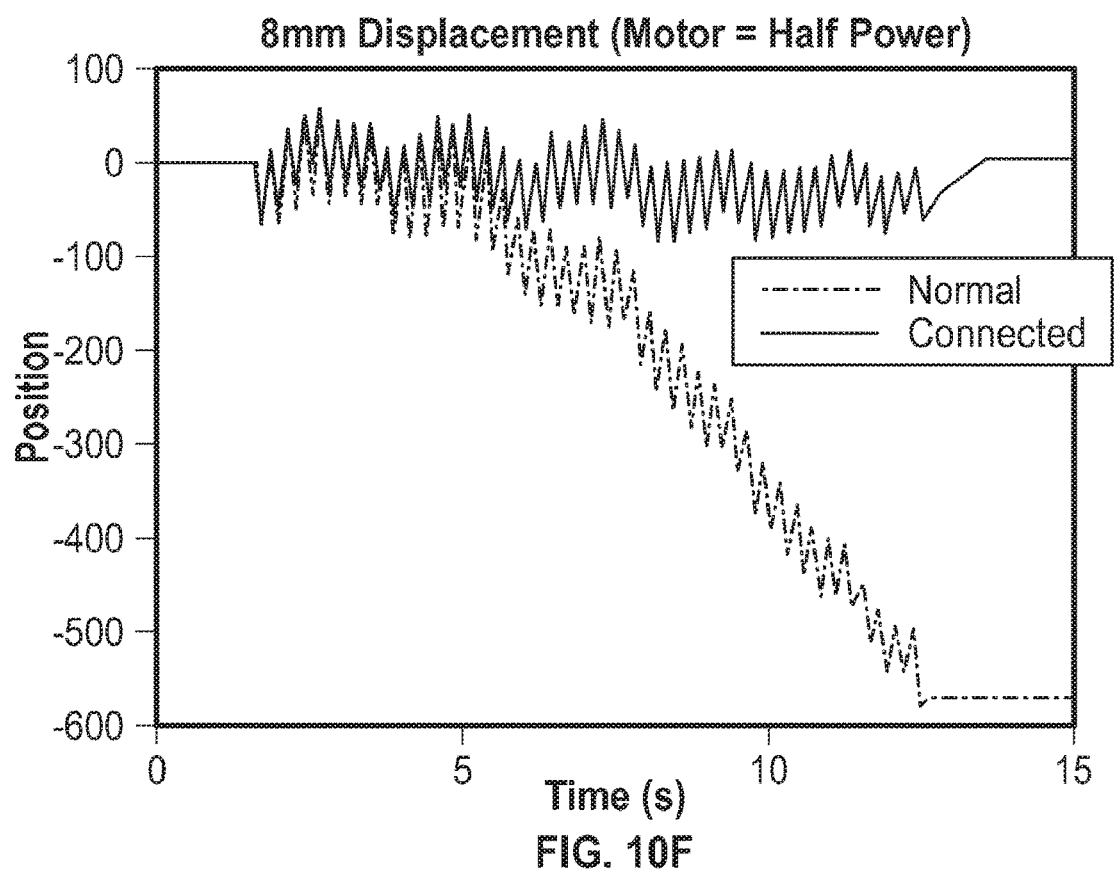
Figure 11A:
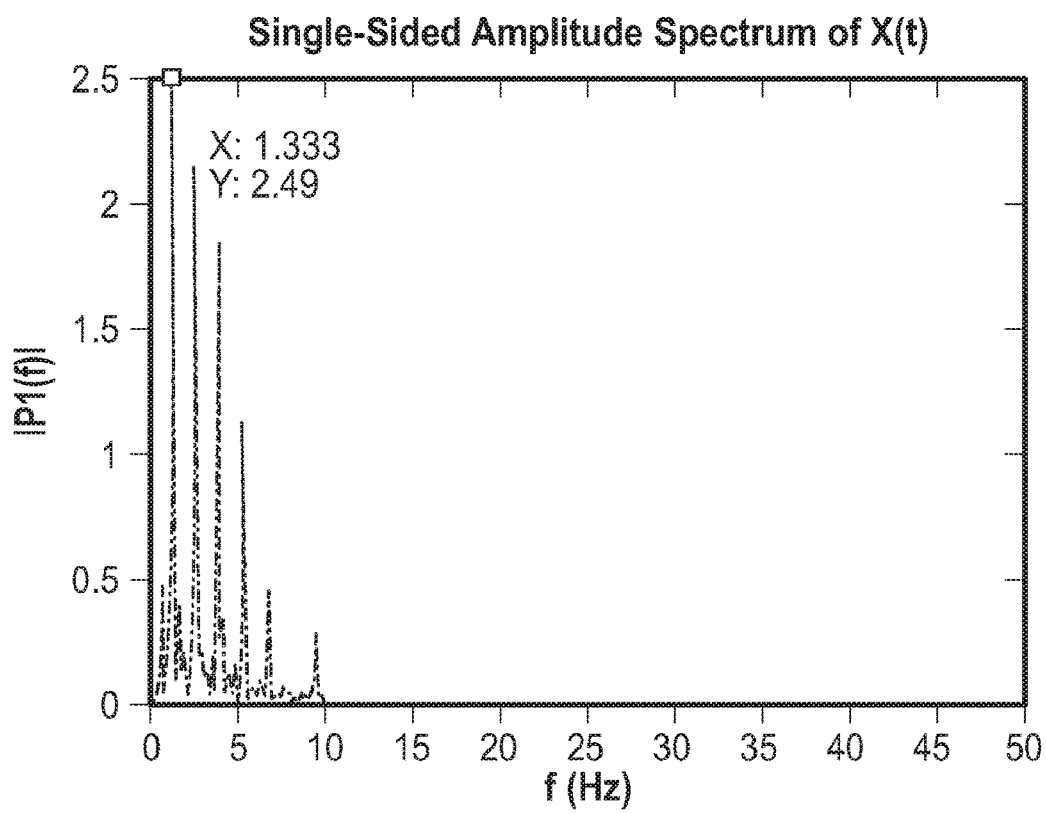
FIGS. 11A-11B show sensor calibration readings of position versus frequency at certain settings, as may be employed in embodiments.
Figure 11B:
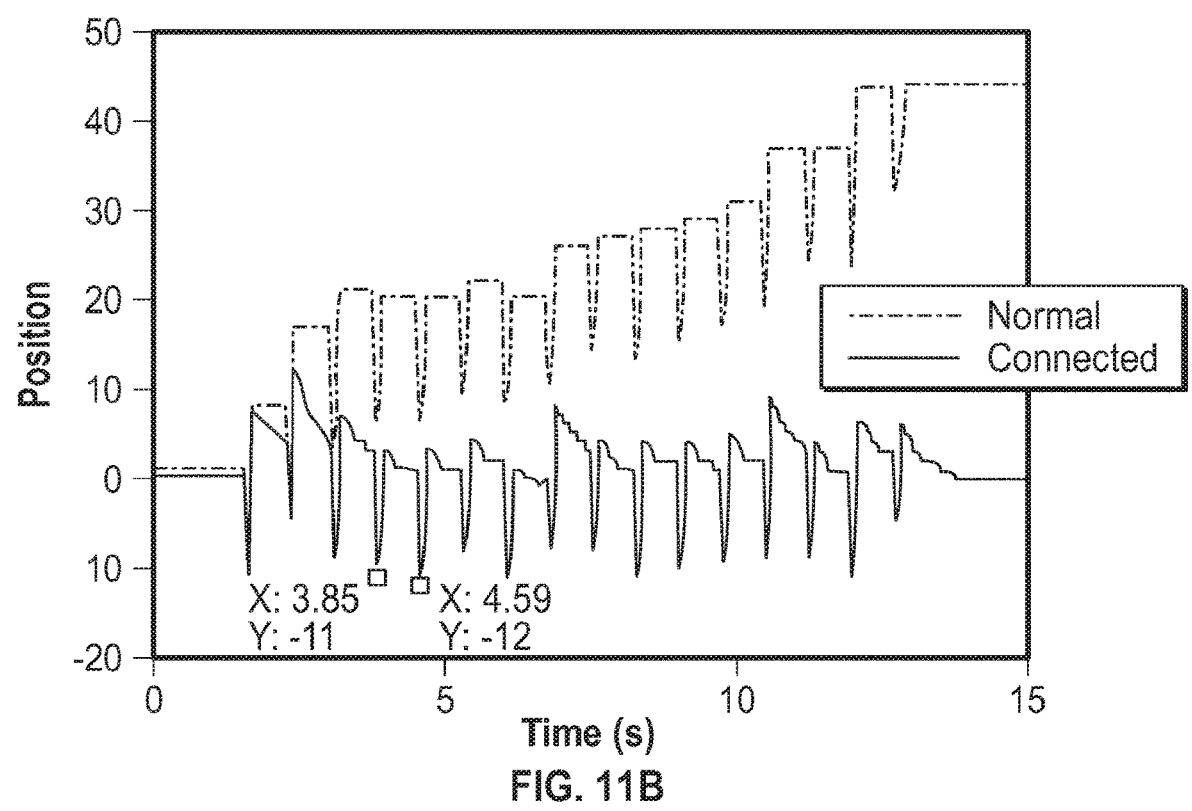
Figure 12A:
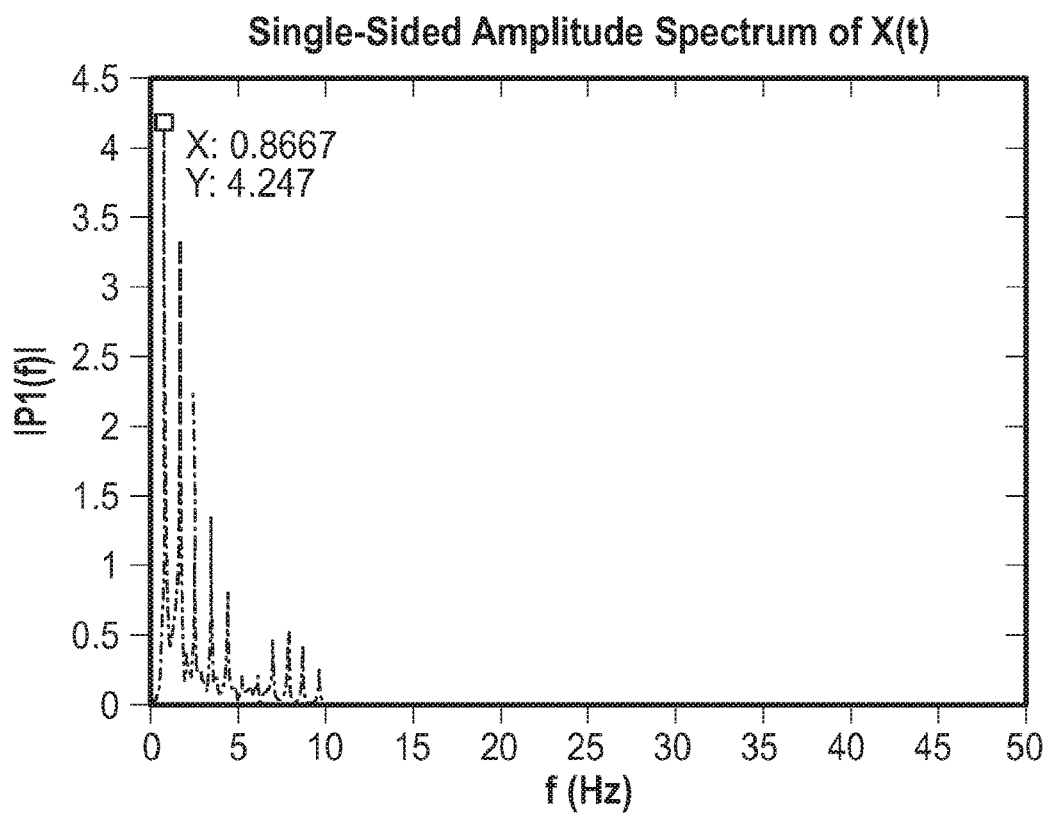
FIGS. 12A-12B show sensor calibration readings of frequency versus position at certain settings, as may be employed in embodiments.
Figure 12B:
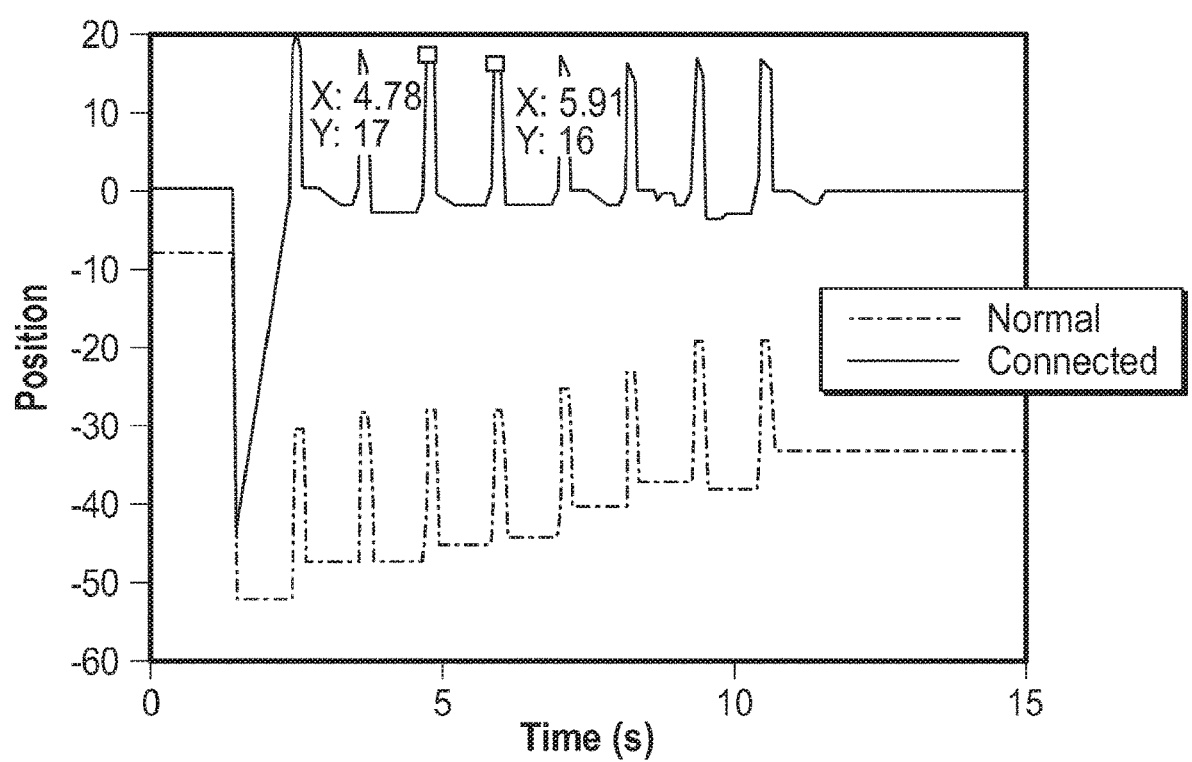
Figure 13A:
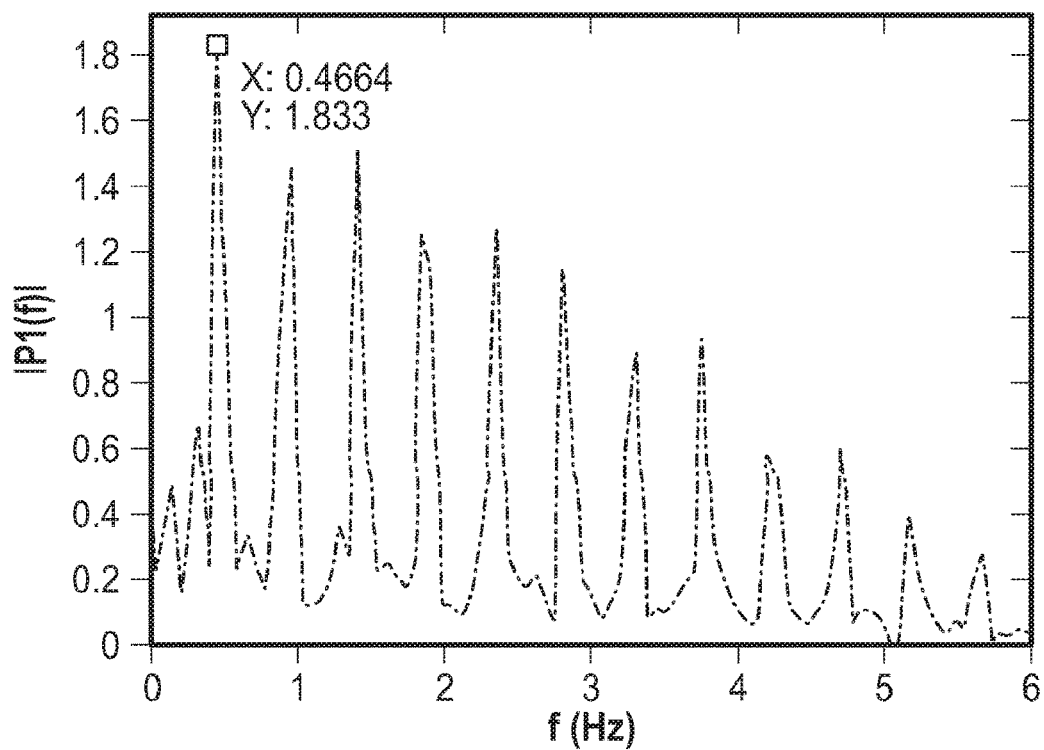
FIGS. 13A-13B show sensor calibration readings of frequency versus position at certain settings, as may be employed in embodiments.
Figure 13B:
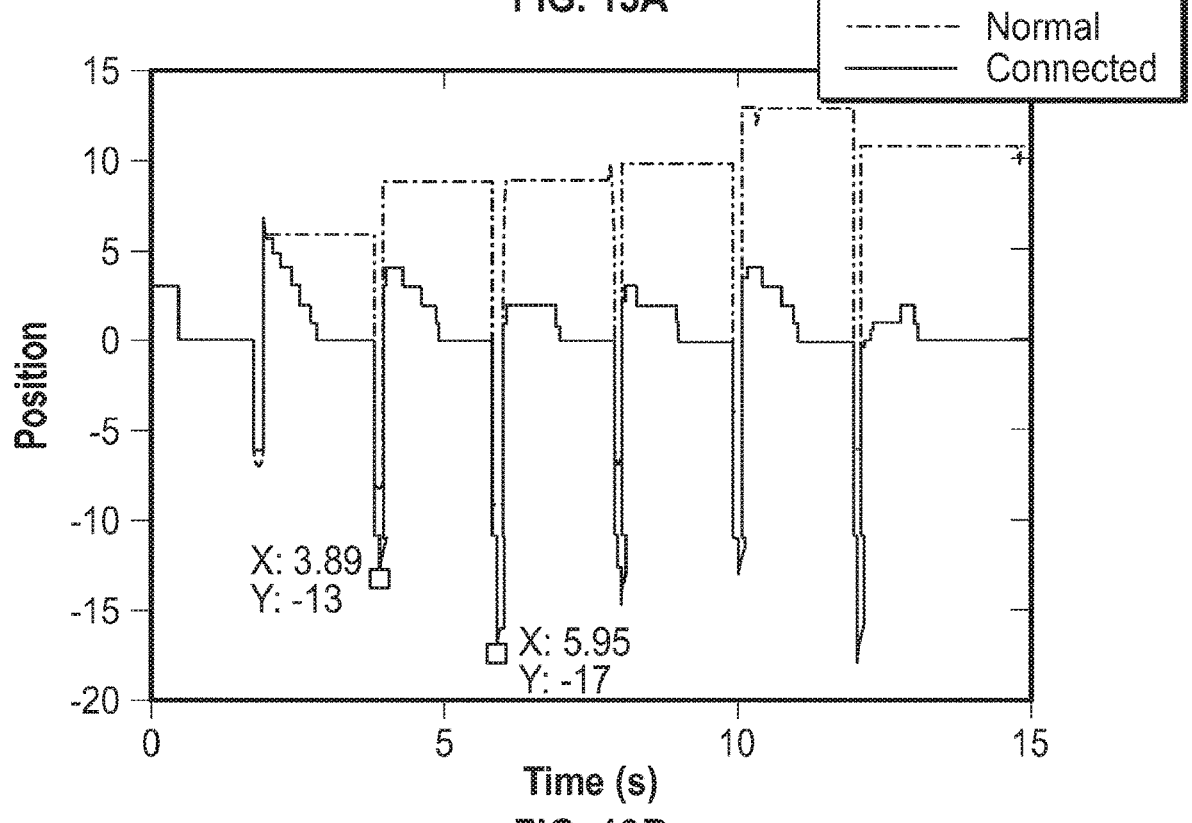

FIG. 6 illustrates the relationship between the absolute position and a unit-less parameter that is a result of the addition of deltas in order to assess the limits of detection and accuracy of the sensor. This data is tabulated in Table 2. Since the relationship between delta and distance is not regularly reported by manufacturers, this relationship was established empirically. It was determined that one unit of displacement is approximately 0.05 mm. Some empirical observations revealed that the tab displacement did not typically exceed one centimeter between the two fixing points. Increasing the distance between them would in turn increase the total displacement of the tab, but a tradeoff of wearability would be needed as it would start approaching the form factor of a chest strap. These calibration techniques may be used for other optical sensors as well.

TABLE 2

| Readings | Total Displacement | mm/reading |
|---|---|---|
| 38 | 1.95 | 0.0513 |
| 40 | 2.36 | 0.0590 |
| 49 | 2.57 | 0.0524 |
| 57 | 2.76 | 0.0484 |
| 109 | 6.21 | 0.0570 |
| 325 | 17.49 | 0.0538 |
| | | 0.0537 |

Detection and Calibration of Optical Sensors for Subsequent Use

Testing to assess the limits of detection and the accuracy of employed sensors may also consist of six 15-seconds runs with a set of motor settings and displacement combinations (full and half power for motor, and 2, 4, and 8 mm). Approximately 30 seconds runs of different breathing patterns may be tested with results saved and plotted accordingly. The results of these calibration tests are shown in FIGS. 7A-18. The steps for these sensor calibrations may include the following:
1. Connect the mouse to the Arduino board with preloaded mouse_position file. Also, connect the sensor prototype to Arduino and then place on the chest with the electrodes positioned in opposite sides of the sternum bone.
2. Open command line interface (CLI from this point forward) and go to the directory where the python script is.
3. Run tests:
Make sure the mouse and the Arduino board are properly connected. Run Serial Monitor (CTRL+SHIFT+m) in Arduino IDE to check this.
Enter r in the prompt area and press enter. Practitioners can see the readings coming in to the serial monitor.

(Practitioners may need to modify the python script to match the baud rate and the port that is being used.)

For each subject:

3.1 Modify the settings for the motor in the Python script accordingly and upload the file. These settings would normally be PORT in which the Arduino is connected and the BAUD rate.

3.2 Run the python script. The format for the run at CLI is "python readSerial.py "nameofthefile.txt""

3.3 At prompt the practitioner can use this option:
y for start test
n for exit script (the script exits automatically after the test is run)

3.4 Be sure to press enter and start the stopwatch at the same time (to the best of the practitioner's ability)

3.5 Indicate the subject to follow the next pattern. Have someone (or the practitioner) dictate when to change patterns and
and when the test is over.

3.6 Wait for the script to display "Done!"

5. Copy the text files from the location where they were stored (same directory where the python script is) to the folder where they are desired to be stored.

6. Open MATLAB and run the MATLAB script. The practitioner can give the directory where the files are. This script will plot and save the figures in the same directory where the text files are.

Calibration operations may consist of a set of runs that use different combinations of motor power and displacements. Prior to establishing these settings, some testing with the motor may be conducted to determine the equivalency for 2 mm, 4 mm, and 8 mm. Those settings may be chosen to demonstrate incremental displacements setting the lower value to 2 mm due to motor limitations. Any value below 2 mm may not be reliable as the resolution of the motor's movements may not allow for consistent displacements. The other two values may be chosen to be able to inspect the ratios between displacements and recorded amplitudes. As seen in FIGS. 7A-9B, a periodic pattern can be identified. Moreover, these patterns are approximately proportional to the set distance. This indicates that at small displacements the sensor is accurate enough to establish a periodic movement pattern which is critical for the application. However, it is also visible that there is some degree of errors as the reading does not go back to baseline every time that the pattern is repeated. Instead, a drift is evident and a solution was required to diminish its effect. An offset reduction algorithm may be implemented when calibration results are similar. This offset algorithm may consist of calculating a running average and subtracting it from each sample.

Offset Algorithm Calibration

The graphs of FIGS. 10A-10F illustrate results for offset algorithm calibration as may be employed in embodiments for calibration or subsequent operation. The graphs show the same runs from the calibration shown above but with both the normal and corrected readings after applying the algorithm. The effectiveness of the offset algorithm may be confirmed when it is shown that readings are kept around the baseline. The number of samples used to calculate the average affect the settling time of the readings. A small number of samples makes the effect of the algorithm more aggressive and in turn settles faster. On the other hand, including more samples increase the settling time. It is important to take this into consideration given that these behaviors could ultimately affect a physiological observation.

Calibration for Displacement-Pause Patterns

Embodiments may also include calibration of different displacement-pause patterns to verify the frequency spectrum and whether artifacts due to system limitations obscured the pattern frequency for calibration and subsequent use. Periods to be analyzed may be set at 0.5, 1 and 2 seconds. These calibration embodiments may be carried out to confirm whether a selected sensor can correctly determine different frequencies of periodic movements. In carrying out these calibrations, an FFT may be applied to the displacement readings to determine the frequency components and verify that they match the period of the movement that was being observed. A 0.5 to 1 Hz band pass filter may be applied beforehand. The selected times may be 0.5 seconds, 1 second and 2 seconds, which correspond to 2, 1 and 0.5 Hz, respectively. The required band of frequency for respiratory rate monitoring goes from 0.0625 to 1 Hz. See, Zhang X, Ding Q. Respiratory rate monitoring from the photoplethysmogram via sparse signal reconstruction. Physiological Measurement. 2016; 37(7):1105-19, which is incorporated by reference in its entirety. Two of the selected values are preferably within the desired band and one may be used as a dummy to inspect the performance of the sensor at a slightly higher frequency. The results are shown in FIGS. 11A-13B. When carrying out the calibration, it is possible to observe that the most prominent frequency peaks match the period of the movements. One important aspect to be considered is that there are some other frequency components that are present. These could be used in embodiments to accommodate an algorithm that inadvertently seems to be introducing some artifacts due to the time that it takes for it to settle. Also, it may be necessary to remove the filter for the 0.5 Hz run due to a discrepancy between the selected period and the actual period that was performed by the motor.

Physiological Observation Calibration to Determine System Performance

Embodiments may also include calibration on a subject to determine embodiments' performance in a physiological observation. These calibration tests may include instructing a subject to follow a sequence of breathing patterns for a period of 30 seconds. The pattern is preferably five seconds of apnea, five seconds of fast breathing, ten seconds of normal breathing, five seconds of fast breathing and five seconds of apnea. Physiological performance observation may follow. Thus, a sequence of breathing patterns was followed and recorded to verify the behavior of the sensor. This calibration may be targeted to determine if a sensor presents an observable difference between specific patterns of respiration.

Figure 14:
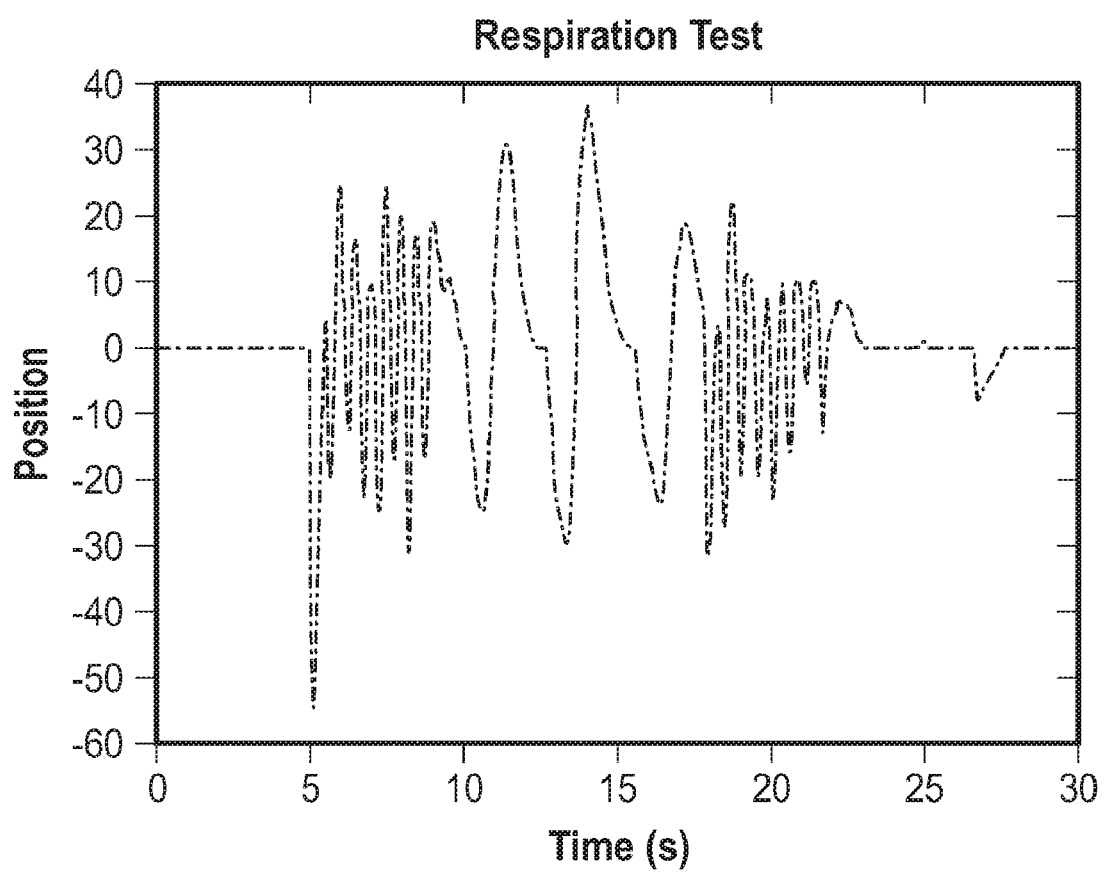
FIG. 14 shows a respiration calibration test result with time versus sensor position, as may be employed in embodiments.

This calibration sequence may include placing a sensor on a subject's chest and holding it in place with the aid of clinical grade electrodes. FIG. 14 shows the results of the 30 second test. In FIG. 14, the breathing patterns that were followed were: apnea, fast breathing, normal breathing, fast breathing, apnea, as may be employed in embodiments. As can be seen, the different patterns are readily apparent, making it possible to observe the transitions to each breathing pattern and confirm the calibration of a sensor.

Oscillation Calibration

Figure 15:
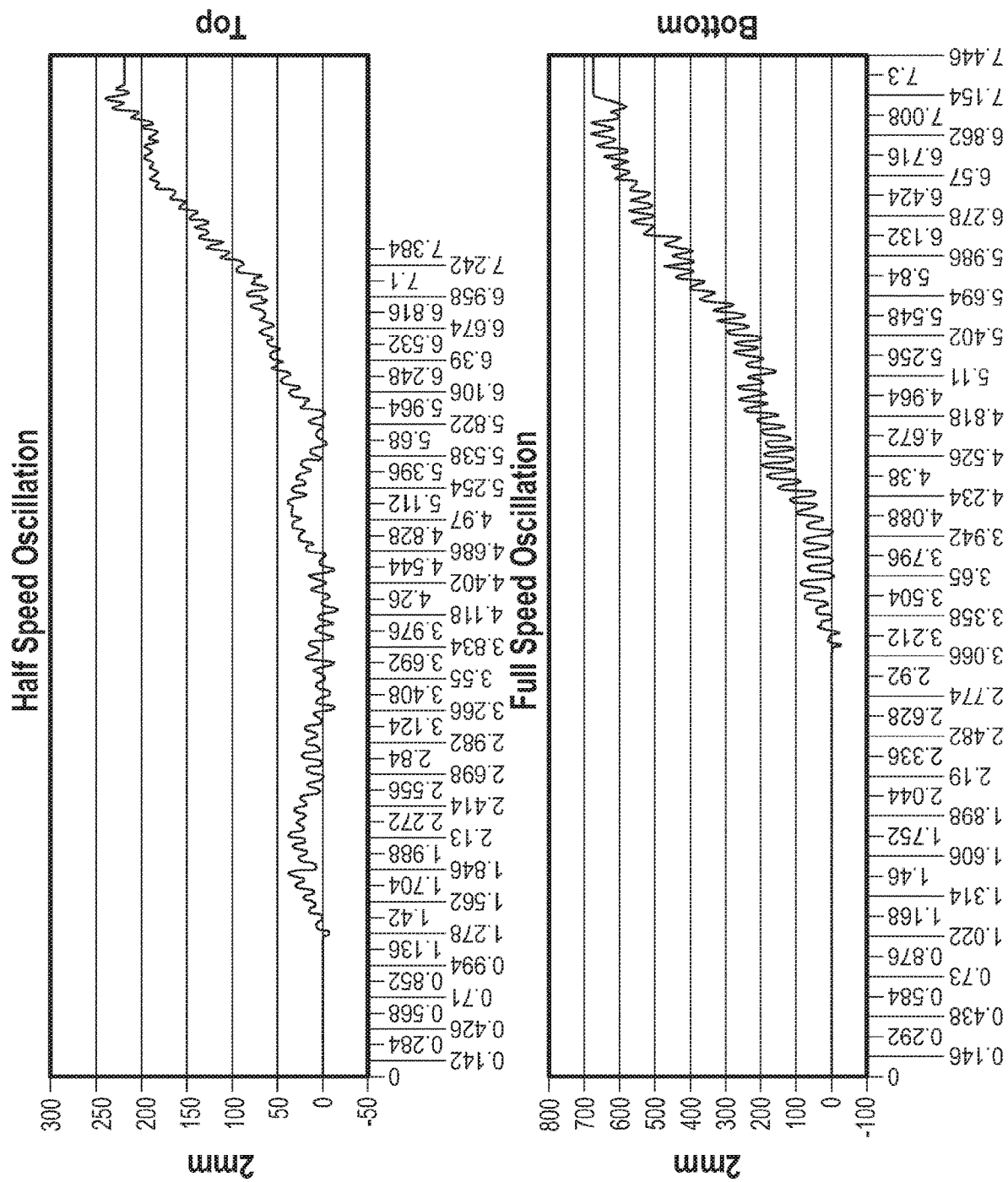
FIGS. 15, 16, and 17 show position versus time plots resulting from sensor calibration readings with motor at half and full speed oscillations, as may be employed in embodiments.
Figure 16:
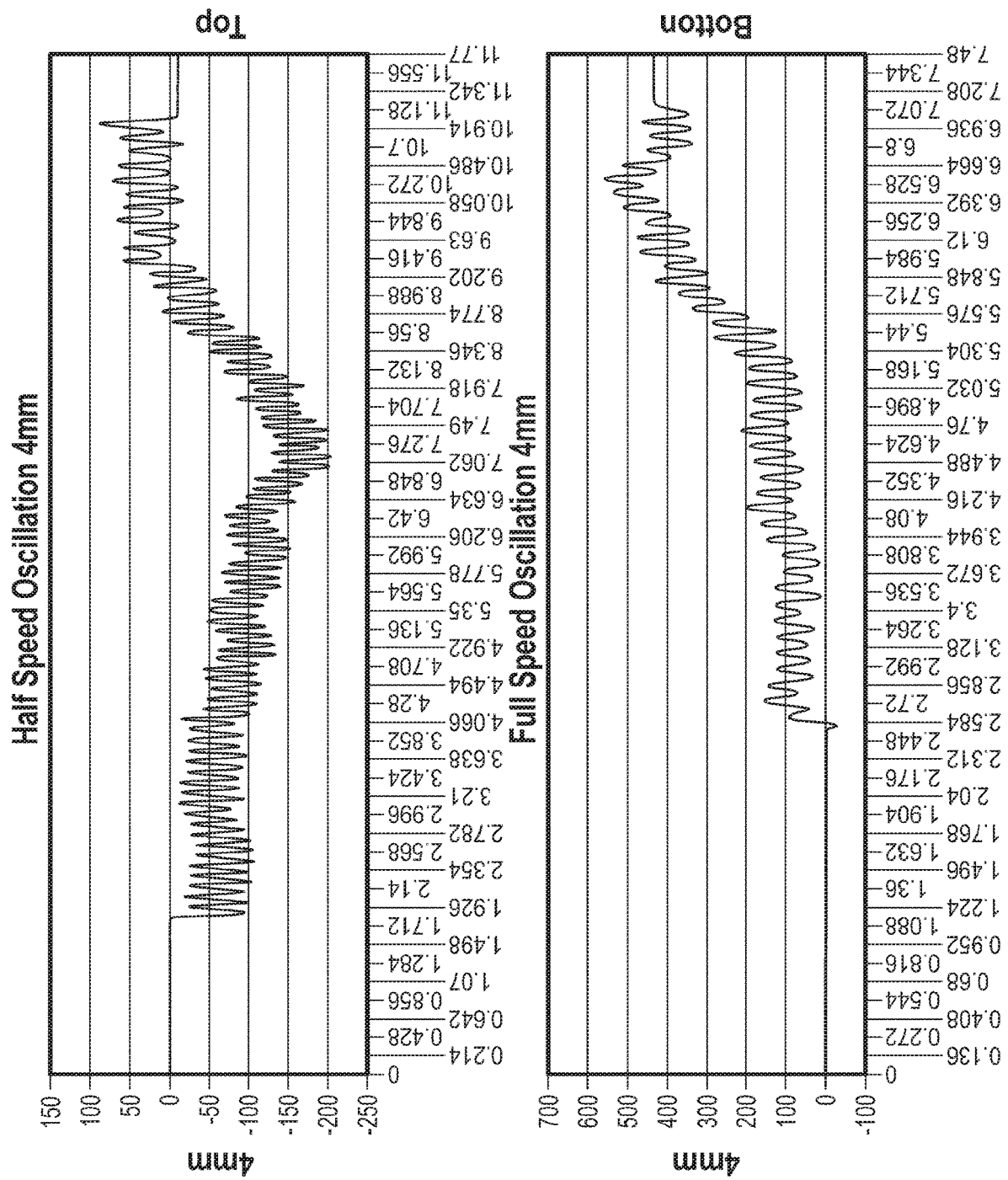
Figure 17:
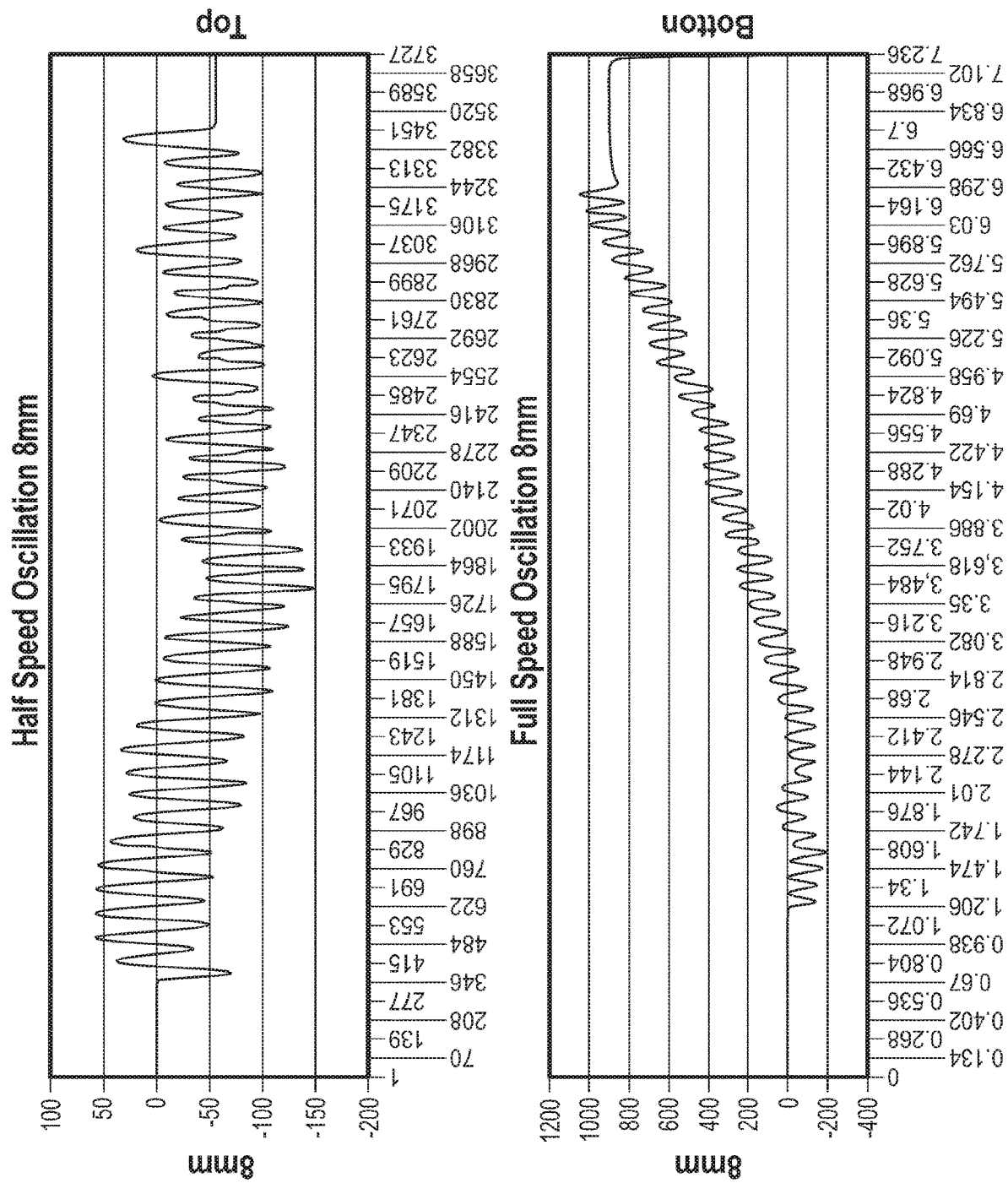

FIGS. 15, 16 and 17, show position versus time plots resulting from the sensor readings with motor at half and full speed oscillations as may be performed when calibrating different oscillation speeds and for subsequent use. FIGS. 15, 16, and 17 demonstrate that detection in certain embodiments may be proportional to the amount of movement detected, as may be employed in embodiments. Calibration testing may be performed by fixing a sensor on top of the testing apparatus described above and performing movements equal to 2, 4, and 8 mm at two different motor speeds. A periodic pattern may be identified and when these patterns are approximately proportional to the set distance, this indicates that at small displacements the sensor is accurate enough to establish a periodic movement pattern.

Figure 18:
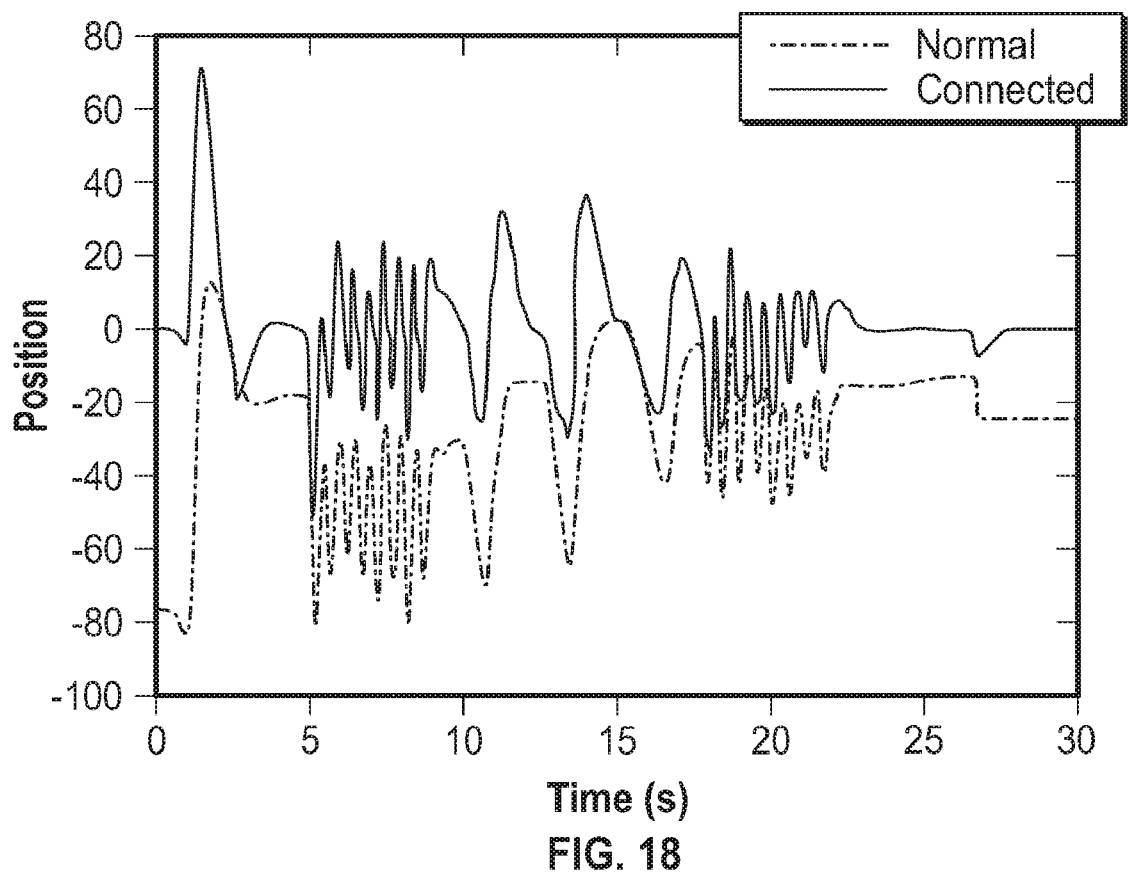
FIG. 18 shows sensor readings of position versus time for a physiological test serving to detect different modes of breathing, as may be employed in embodiments.

FIG. 18 shows a physiological test where position versus time is graphed for normal and corrected values. FIG. 18 provides position versus time for a physiological test serving to detect different modes of breathing, as may be employed in embodiments. Different modes of breathing were simulated and tested during the test reflected in FIG. 18.

Arduino Code that may be Employed in Calibration/Testing

```
#include <SPI.h>
#include "RunningAverage.h"
RunningAverage myRA(100);
int samples = 0;
char userInput;
int SCLK = 5;
int SDIO = 6;
int NCS =7;
int delta_x, delta_y;
int pos = 0;
int posCorrected;
unsigned long start_time, stop_time;
void setup( ) {
    Serial.begin(9600);
    pinMode(SCLK, OUTPUT);
    pinMode(SDIO, OUTPUT);
    pinMode(NCS, OUTPUT);
    myRA.clear( );
    mouse_reset( );
    delay(10);
}
void loop( ) {
    if(Serial.available( ) > 0) {
        userInput = Serial.read( );
        if(userInput == 'r') {
            pos = 0; // initialize position
            myRA.clear( ); // initialize running average array
            //start_time = millis( );
            //stop_time = millis( );
            for(int i = 0; i < 3000; i++){
                delta_x = changeSign(readLoc(0x03)); //
                recommended to read both every time
                delta_y = changeSign(readLoc(0x04));
                pos += delta_y;
                myRA.addValue(pos);
                posCorrected = pos - myRA.getAverage( );
                Serial.print(pos);
                Serial.print("\t");
                Serial.println(posCorrected);
                delay(10);
            }
        }
    }
}
void mouse_reset( ){
    // Initiate chip reset
    digitalWrite(NCS, LOW);
    pushbyte(0x3a);
    pushbyte(0x5a);
    digitalWrite(NCS, HIGH);
    delay(10);
    // Set 1000cpi resolution
    digitalWrite(NCS, LOW);
    pushbyte(0x0d);
    pushbyte(0x01);
    digitalWrite(NCS, HIGH);
}
unsigned int readLoc(uint8_t addr){
    int ret=0;
    digitalWrite(NCS, LOW);
    pushbyte(addr);
    ret=pullbyte( );
    digitalWrite(NCS, HIGH);
    return(ret);
}
void pushbyte(uint8_t c){
    pinMode(SDIO, OUTPUT);
    for(unsigned int i=0x80;i;i=i>>1){
        digitalWrite(SCLK, LOW);
        digitalWrite(SDIO, c & i);
        digitalWrite(SCLK, HIGH);
    }
}
unsigned int pullbyte( ){
    unsigned int ret=0;
    pinMode(SDIO, INPUT);
    for(unsigned int i=0x80; i>0; i>>=1) {
        digitalWrite(SCLK, LOW);
        ret |= i*digitalRead(SDIO);
        digitalWrite(SCLK, HIGH);
    }
    pinMode(SDIO, OUTPUT);
    return(ret);
}
int changeSign(unsigned int x) {
    if (x <= 128) {
        return x;
    }
    else {
        return x-256;
    }
}
```

Python Script that May Be Employed in Calibration/Testing

```
import serial
import time
from sys import argv
script, file_name = argv
# function to acquire a values from arduino
def getValues(points):
    ser.write(b'r')
    dataPoints = [ ]
    for i in range(0, points):
        line = ser.readline( ).decode("utf-8")
        # print(line)
        dataPoints.append(line)
    return dataPoints
# initialize lists and variables
numPoints = 3000
dataList = [ ]
# create and open serial
ser = serial.Serial('COM7', baudrate = 9600, timeout = 1)
time.sleep(3) # wait for 3 seconds to 'fully initialize' arduino
# enter test loop
while True:
    # ask user for input
    userInput = str(raw_input("Start test (y/n)?"))
    # main process of gathering data and creating
    if userInput == "y":
        # open/create file name and set it to write
        output_file = open(file_name, 'w')
        # get values from arduino and store in dataList
        dataList = getValues(numPoints)
```

| Python Script that May Be Employed in Calibration/Testing |
|---|
| ```
            # write values to output file
            for i in dataList:
                output_file.write(i)
            # close file and close serial port
            output_file.close( )
            ser.close( )
            print("Done!")
            # exit loop and program
            break
        elif userInput == "n":
            # exit program
            break
        else:
            # print error msg and ask again
            print("I did not get that!")
``` |

| MATLAB Script that May Be Employed in Calibration/Testing |
|---|
| ```
function plotFolder(name) %Get the directory name as an argument
%-------------------------FIND FILES--------------------------------------
    %Change working directory accordingly
    cd(name);
    %Find all the .txt files in it
    files = dir('**/*.txt');
    %Create an array that has all the names in a way I can use it to
    %iterate through them
    filesNames = cell2mat({files.name}');
    %%%NOTE: there's a bug that will make this fail if the file names
    are of
    %%%different name. Needs to be fixed.
    %Get number of files in filesNames to control FOR loop
    numberOfFiles = size(filesNames,1);
    %ITERATE THROUGH FILES
    for I = 1:numberOfFiles
        %Get Ith file name to use through iteration
        iterationName = filesNames(I,:);
        %Import data from file
        A = importdata(iterationName);
        sizeArray = size(A);
%-------------------------CALCULATIONS------------------------------------
%-------------------------PLOTS------------------------------------------
        %Create degrees for x-axis label
        interval = 0.01;
        lastPoint = (sizeArray(1) − 1) * interval;
        time = (0:interval:lastPoint)';
        %Create new figure from iterationName
        figureName = iterationName(1,1:end−4);
        figure('Name',figureName);
        %Set hold on to keep all plots in same figure
        hold on;
        %Plot each column
        for i=1:sizeArray(2)
            plot(time, A(:,i), '—');
        end
        %Edit figure settings
        legend('Normal','Corrected');
        xlabel('Time (s)');
        ylabel('Position');
        %Save figure
        savefig(figureName);
    end
end
function calculateFFT(array,filt,Fs)
    xf = filter(filt,array);
    L = length(array);
    Y = fft(xf);
    P2 = abs(Y/L);
    P1 = P2(1:(L/2)+1);
    P1(2:end−1) = 2*P1(2:end−1);
    f = Fs*(0:(L/2))/L;
    plot(f,P1)
``` |

| MATLAB Script that May Be Employed in Calibration/Testing |
|---|
| ```
    title('Single-Sided Amplitude Spectrum of X(t)')
    xlabel('f (Hz)')
    ylabel(' | P1(f) | ')
end
``` |

While embodiments have been illustrated herein, they are not intended to restrict or limit the scope of the appended claims to such detail. In view of the teachings in this application, additional advantages and modifications will be readily apparent to and appreciated by those having ordinary skill in the art. Accordingly, changes may be made to the above embodiments without departing from the scope of the invention.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the terms "about" or "approximately" in reference to a recited numeric value, including for example, whole numbers, fractions, and/or percentages, generally indicates that the recited numeric value encompasses a range of numerical values (e.g., +/−5% to 10% of the recited value) that one of ordinary skill in the art would consider equivalent to the recited value (e.g., performing substantially the same function, acting in substantially the same way, and/or having substantially the same result). It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Certain embodiments may be implemented as a computer process, a computing system or as an article of manufacture such as a computer program product of computer readable media. The computer program product may be a computer storage medium readable by a computer system and encoding computer program instructions for executing a computer process.

The corresponding structures, material, acts, and equivalents of any means or steps plus function elements in the claims are intended to include any structure, material or act for performing the function in combination with other claimed elements. The description of certain embodiments of the present invention have been presented for purposes of illustration and description, but is not intended to be exhaustive or limited to the invention in the form disclosed. Many modifications and variations will be apparent to those of ordinary skill without departing from the scope and spirit of the invention. These embodiments were chosen and described in order to best explain the principles of the invention and the practical application, and to enable others of ordinary skill in the art to understand the invention for embodiments with various modifications as are suited to the particular use contemplated.

What is claimed is:

1. A device for monitoring a respiration rate of a wearer, comprising:
a first attachment point configured to be removably attached to the wearer; and
a second attachment point configured to be removably attached to the wearer;
the first and second attachment points being connected by a tab, the tab being fixedly attached to the first attachment point and slidably connected to the second attachment point,
wherein the second attachment point houses an optical sensor configured to sense movement of the tab and generate output signals based on the sensed movement of the tab,
wherein the output signals from the optical sensor are sent to a microprocessor, the microprocessor configured to determine a respiratory status of the wearer based on the output signals received from the optical sensor,
wherein the microprocessor is further configured to filter mechanical noise by creating an average of a set of signals received from the optical sensor and subtracting the average from each subsequent signal received from the optical sensor for a subsequent predetermined period of time or cycles, and
wherein the microprocessor is further configured to identify one or more differences in subsequent signals received from the optical sensor, add the one or more differences to a container variable, and calculate an absolute difference for a predetermined subsequent period of time or cycles.

2. The device of claim 1, wherein the second attachment point further comprises:
a data storage device;
an optical display; and
a bus configured to provide a communication path for the data storage device, the sensor, the microprocessor, and the optical display.

3. The device of claim 2, wherein the second attachment point further comprises a communications unit coupled to the bus, the communications unit configured to provide wireless output of signals from the microprocessor.

4. The device of claim 1, wherein the tab has an elongated flattened shape and wherein the slidable connection between the tab and the second attachment point restricts movement along a z-axis but allows movement along an x-axis and a y-axis.

5. The device of claim 1, wherein the microprocessor is further configured to identify an offset reduction by determining a running average for a received signal from the optical sensor and subtracting that running average from every subsequent signal received from the optical sensor for a predetermined subsequent period of time or cycles.

6. The device of claim 1, wherein the microprocessor is further configured to calculate the frequency of a waveform sensed by the optical sensor and determine peak lengths of each sensed waveform.

7. A system for monitoring a respiration rate of a wearer, comprising:
a first attachment point configured to be removably attached to the wearer; and
a second attachment point configured to be removably attached to the wearer;
the first and second attachment points being connected by a tab, the tab being fixedly attached to the first attachment point and slidably connected to the second attachment point,
wherein the second attachment point houses an optical sensor configured to sense movement of the tab and generate output signals based on the sensed movement of the tab,
wherein the output signals from the optical sensor are sent to a microprocessor, the microprocessor configured to determine a respiratory status of the wearer based on the output signals received from the optical sensor,
wherein the microprocessor is further configured to filter mechanical noise by creating an average of a set of signals received from the optical sensor and subtracting the average from each subsequent signal received from the optical sensor for a subsequent predetermined period of time or cycles, and
wherein the microprocessor is further configured to identify one or more differences in subsequent signals received from the optical sensor, add the one or more differences to a container variable, and calculate an absolute difference for a predetermined subsequent period of time or cycles.

8. The system of claim 7, wherein the second attachment point further comprises:
a data storage device;
an optical display; and
a bus configured to provide a communication path for the data storage device, the sensor, the microprocessor, and the optical display.

9. The system of claim 8, wherein the second attachment point further comprises a communications unit, the communications unit coupled to the bus, the communications unit configured to provide wireless output of signals from the microprocessor.

10. The system of claim 7, wherein the tab has an elongated flattened shape and wherein the slidable connection between the tab and the second attachment point restricts movement along a z-axis but allows movement along an x-axis and a y-axis.

11. The system of claim 7, wherein the microprocessor is further configured to identify an offset reduction by determining a running average for a received signal from the optical sensor and subtracting that running average from every subsequent signal received from the optical sensor for a predetermined subsequent period of time or cycles.

12. The system of claim 7, wherein the microprocessor is further configured to calculate the frequency of a waveform sensed by the optical sensor and determine peak lengths of each sensed waveform.

\* \* \* \* \*